(12) United States Patent
Friend et al.

(10) Patent No.: US 8,709,078 B1
(45) Date of Patent: Apr. 29, 2014

(54) OCULAR IMPLANT WITH SUBSTANTIALLY CONSTANT RETINAL SPACING FOR TRANSMISSION OF NERVE-STIMULATION LIGHT

(75) Inventors: Michael E. Friend, Seattle, WA (US); Yongdan Hu, Bothell, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 59 days.

(21) Appl. No.: 13/204,610

(22) Filed: Aug. 5, 2011

Related U.S. Application Data

(60) Provisional application No. 61/514,894, filed on Aug. 3, 2011.

(51) Int. Cl.
  *A61F 2/14* (2006.01)
(52) U.S. Cl.
  USPC ........ 623/5.11; 623/6.11; 623/6.34; 623/6.63
(58) Field of Classification Search
  USPC ........................ 623/4.1, 5.11, 6.11, 6.63, 6.34
  See application file for complete search history.

(56) References Cited

U.S. PATENT DOCUMENTS

| | | |
|---|---|---|
| 4,064,872 A | 12/1977 | Caplan |
| 4,215,694 A | 8/1980 | Isakov et al. |
| 4,232,678 A | 11/1980 | Skovajsa |
| 4,296,995 A | 10/1981 | Bickel |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,720,189 A | 1/1988 | Heynen et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |

(Continued)

FOREIGN PATENT DOCUMENTS

| | | |
|---|---|---|
| WO | WO 0025112 | 5/2000 |
| WO | WO 2010011404 A2 | 1/2010 |

OTHER PUBLICATIONS

Huang, Ying-Ying, et al., "Biphasic Dose Response in Low Level Light Therapy", "Dose-Response", 2009, pp. 358-383, vol. 7.

(Continued)

*Primary Examiner* — David Isabella
*Assistant Examiner* — Randy Shay
(74) *Attorney, Agent, or Firm* — Charles A. Lemaire; Jonathan M. Rixen; Lemaire Patent Law Firm, P.L.L.C.

(57) ABSTRACT

An improved prosthesis and method for stimulating vision nerves to obtain a vision sensation that is useful for the patient that has lost vision due to age-related macular degeneration (AMD) and retinitis pigmentosa (RP) and other diseases. The present invention utilizes infrared light to cause action potentials in the retinal nerves similar to those which result from rods and cones stimulated by visible light in healthy retinas. In some embodiments, the invention provides a pathway or "image pipe" for transmitting a stimulation pattern of infrared light from an external stimulator array through the eye and focusing the stimulation pattern of infrared light on the retina, especially the fovea. Some embodiments provide improved resolution down to a group of nerves, or even the individual nerve level, with sufficient energy density so as to cause a desired action potential.

25 Claims, 18 Drawing Sheets

(56) References Cited

U.S. PATENT DOCUMENTS

| | | | |
|---|---|---|---|
| 4,928,695 | A | 5/1990 | Goldman et al. |
| 4,930,504 | A | 6/1990 | Diamantopoulos et al. |
| 4,972,331 | A | 11/1990 | Chance |
| 4,989,605 | A | 2/1991 | Rossen |
| 5,062,428 | A | 11/1991 | Chance |
| 5,088,493 | A | 2/1992 | Giannini et al. |
| 5,122,974 | A | 6/1992 | Chance |
| 5,139,025 | A | 8/1992 | Lewis et al. |
| 5,150,704 | A | 9/1992 | Tatebayashi et al. |
| 5,151,909 | A | 9/1992 | Davenport et al. |
| 5,152,278 | A | 10/1992 | Clayman |
| 5,187,672 | A | 2/1993 | Chance et al. |
| 5,192,278 | A | 3/1993 | Hayes et al. |
| 5,212,386 | A | 5/1993 | Gratton et al. |
| 5,213,093 | A | 5/1993 | Swindle |
| 5,213,105 | A | 5/1993 | Gratton et al. |
| 5,257,202 | A | 10/1993 | Feddersen et al. |
| 5,259,382 | A | 11/1993 | Kronberg |
| 5,261,822 | A | 11/1993 | Hall et al. |
| 5,323,010 | A | 6/1994 | Gratton et al. |
| 5,327,902 | A | 7/1994 | Lemmen |
| 5,353,799 | A | 10/1994 | Chance |
| 5,386,827 | A | 2/1995 | Chance et al. |
| 5,391,202 | A * | 2/1995 | Lipshitz et al. ............... 623/6.34 |
| 5,402,778 | A | 4/1995 | Chance |
| 5,419,312 | A | 5/1995 | Arenberg et al. |
| 5,430,175 | A | 7/1995 | Hess et al. |
| 5,445,146 | A | 8/1995 | Bellinger |
| 5,464,960 | A | 11/1995 | Hall et al. |
| 5,480,482 | A | 1/1996 | Novinson |
| 5,484,432 | A | 1/1996 | Sand |
| 5,548,604 | A | 8/1996 | Toepel |
| 5,553,614 | A | 9/1996 | Chance |
| 5,564,417 | A | 10/1996 | Chance |
| 5,608,519 | A | 3/1997 | Gourley et al. |
| 5,664,574 | A | 9/1997 | Chance |
| 5,704,899 | A | 1/1998 | Milo |
| 5,754,578 | A | 5/1998 | Jayaraman |
| 5,755,752 | A | 5/1998 | Segal |
| 5,792,051 | A | 8/1998 | Chance |
| 5,796,889 | A | 8/1998 | Xu et al. |
| 5,799,030 | A | 8/1998 | Brenner |
| 5,851,223 | A | 12/1998 | Liss et al. |
| 5,899,865 | A | 5/1999 | Chance |
| 5,913,884 | A | 6/1999 | Trauner et al. |
| 6,033,431 | A | 3/2000 | Segal |
| 6,048,359 | A | 4/2000 | Biel |
| 6,055,110 | A | 4/2000 | Kintz et al. |
| 6,066,127 | A | 5/2000 | Abe |
| 6,074,411 | A | 6/2000 | Lai et al. |
| 6,104,957 | A | 8/2000 | Alo et al. |
| 6,110,195 | A | 8/2000 | Xie et al. |
| 6,152,882 | A | 11/2000 | Prutchi |
| 6,171,239 | B1 | 1/2001 | Humphrey |
| 6,184,542 | B1 | 2/2001 | Alphonse |
| 6,224,969 | B1 | 5/2001 | Steenbergen et al. |
| 6,246,892 | B1 | 6/2001 | Chance |
| 6,254,637 | B1 | 7/2001 | Lee et al. |
| 6,257,759 | B1 | 7/2001 | Witonsky et al. |
| 6,258,082 | B1 | 7/2001 | Lin |
| 6,263,221 | B1 | 7/2001 | Chance et al. |
| 6,267,779 | B1 | 7/2001 | Gerdes |
| 6,272,367 | B1 | 8/2001 | Chance |
| 6,284,078 | B1 | 9/2001 | Witonsky et al. |
| 6,294,109 | B1 | 9/2001 | Ratna et al. |
| 6,301,279 | B1 | 10/2001 | Garbuzov et al. |
| 6,310,083 | B1 | 10/2001 | Kao et al. |
| 6,312,451 | B1 | 11/2001 | Streeter |
| 6,314,324 | B1 | 11/2001 | Lattner et al. |
| 6,324,429 | B1 | 11/2001 | Shire et al. |
| 6,330,388 | B1 | 12/2001 | Bendett et al. |
| 6,339,606 | B1 | 1/2002 | Alphonse |
| 6,353,226 | B1 | 3/2002 | Khalil et al. |
| 6,358,272 | B1 | 3/2002 | Wilden |
| 6,363,188 | B1 | 3/2002 | Alphonse |
| 6,391,055 | B1 | 5/2002 | Ikada et al. |
| 6,396,461 | B1 | 5/2002 | Lewis et al. |
| 6,417,524 | B1 | 7/2002 | Alphonse |
| 6,421,474 | B2 | 7/2002 | Jewell et al. |
| 6,444,313 | B1 | 9/2002 | Ono et al. |
| 6,456,866 | B1 | 9/2002 | Tyler et al. |
| 6,459,715 | B1 | 10/2002 | Khalfin et al. |
| 6,468,306 | B1 * | 10/2002 | Paul et al. ..................... 623/6.16 |
| 6,475,800 | B1 | 11/2002 | Hazen et al. |
| 6,488,704 | B1 | 12/2002 | Connelly et al. |
| 6,493,476 | B2 | 12/2002 | Bendett |
| 6,505,075 | B1 | 1/2003 | Weiner |
| 6,542,530 | B1 | 4/2003 | Shieh et al. |
| 6,542,772 | B1 | 4/2003 | Chance |
| 6,546,291 | B2 | 4/2003 | Merfeld et al. |
| 6,556,611 | B1 | 4/2003 | Khalfin et al. |
| 6,564,076 | B1 | 5/2003 | Chance |
| 6,585,411 | B2 | 7/2003 | Hammarth et al. |
| 6,592,611 | B1 | 7/2003 | Zawada |
| 6,630,673 | B2 | 10/2003 | Khalil et al. |
| 6,636,678 | B1 | 10/2003 | Bendett et al. |
| 6,639,930 | B2 | 10/2003 | Griffel et al. |
| 6,669,379 | B2 | 12/2003 | Janosik et al. |
| 6,669,765 | B2 | 12/2003 | Senga et al. |
| 6,688,783 | B2 | 2/2004 | Janosik et al. |
| 6,690,873 | B2 | 2/2004 | Bendett et al. |
| 6,735,474 | B1 | 5/2004 | Loeb et al. |
| 6,735,475 | B1 | 5/2004 | Whitehurst et al. |
| 6,744,548 | B2 | 6/2004 | Abeles |
| 6,746,473 | B2 | 6/2004 | Shanks et al. |
| 6,748,275 | B2 | 6/2004 | Lattner et al. |
| 6,823,109 | B2 | 11/2004 | Sasaki et al. |
| RE38,670 | E | 12/2004 | Asah et al. |
| 6,836,685 | B1 | 12/2004 | Fitz |
| 6,871,084 | B1 | 3/2005 | Kingsley et al. |
| 6,902,528 | B1 | 6/2005 | Garibaldi et al. |
| 6,909,826 | B2 | 6/2005 | Cai et al. |
| 6,920,358 | B2 | 7/2005 | Greenberg et al. |
| 6,921,413 | B2 | 7/2005 | Mahadevan-Jansen et al. |
| 6,953,341 | B2 | 10/2005 | Black |
| 6,956,650 | B2 | 10/2005 | Boas et al. |
| 6,976,997 | B2 | 12/2005 | Noolandi et al. |
| 6,980,579 | B2 | 12/2005 | Jewell |
| 6,989,023 | B2 | 1/2006 | Black |
| 7,003,353 | B1 | 2/2006 | Parkhouse |
| 7,004,645 | B2 | 2/2006 | Lemoff et al. |
| 7,006,749 | B2 | 2/2006 | Illich et al. |
| 7,010,341 | B2 | 3/2006 | Chance |
| 7,010,356 | B2 | 3/2006 | Jog et al. |
| 7,031,363 | B2 | 4/2006 | Biard et al. |
| 7,040,805 | B1 | 5/2006 | Ou et al. |
| 7,068,878 | B2 | 6/2006 | Crossman-Bosworth et al. |
| 7,069,083 | B2 | 6/2006 | Finch et al. |
| 7,079,900 | B2 | 7/2006 | Greenburg et al. |
| 7,085,300 | B2 | 8/2006 | Werner et al. |
| 7,095,770 | B2 | 8/2006 | Johnson |
| 7,116,886 | B2 | 10/2006 | Colgan et al. |
| 7,131,968 | B2 | 11/2006 | Bendett et al. |
| 7,133,022 | B2 | 11/2006 | Grabert |
| 7,139,603 | B2 | 11/2006 | Chance |
| 7,156,866 | B1 | 1/2007 | Riggs et al. |
| 7,160,289 | B2 | 1/2007 | Cohen |
| 7,177,081 | B2 | 2/2007 | Tomita et al. |
| 7,190,993 | B2 | 3/2007 | Sharma et al. |
| 7,194,063 | B2 | 3/2007 | Dilmanian et al. |
| 7,225,028 | B2 | 5/2007 | Della Santina et al. |
| 7,231,256 | B2 | 6/2007 | Wahlstrand et al. |
| 7,244,253 | B2 | 7/2007 | Neev |
| 7,302,296 | B1 | 11/2007 | Hoffer |
| 7,311,722 | B2 | 12/2007 | Larsen |
| 7,311,723 | B2 * | 12/2007 | Seibel et al. ..................... 607/89 |
| 7,324,852 | B2 | 1/2008 | Barolat et al. |
| 7,329,251 | B2 | 2/2008 | Yamada et al. |
| 7,337,004 | B2 | 2/2008 | Classen et al. |
| 7,351,241 | B2 | 4/2008 | Bendett et al. |
| 7,391,561 | B2 | 6/2008 | Di Teodoro et al. |
| 7,402,167 | B2 | 7/2008 | Nemenov |
| 7,488,341 | B2 | 2/2009 | Merfeld |
| 7,647,112 | B2 | 1/2010 | Tracey et al. |

(56) References Cited

U.S. PATENT DOCUMENTS

| | | | |
|---|---|---|---|
| 7,654,750 | B2 | 2/2010 | Brenner et al. |
| 7,736,382 | B2 | 6/2010 | Webb et al. |
| 7,747,318 | B2 | 6/2010 | John et al. |
| 7,756,588 | B2 | 7/2010 | Jog et al. |
| 7,776,631 | B2 | 8/2010 | Miles |
| 7,787,170 | B2 | 8/2010 | Patel et al. |
| 7,792,588 | B2 | 9/2010 | Harding |
| 7,797,029 | B2 | 9/2010 | Gibson et al. |
| 7,801,601 | B2 | 9/2010 | Maschino et al. |
| 7,803,454 | B2 | 9/2010 | Toepel |
| 7,833,257 | B2 | 11/2010 | Walsh, Jr. et al. |
| 7,857,849 | B2 | 12/2010 | Myung et al. |
| 7,873,085 | B2 | 1/2011 | Babushkin et al. |
| 7,883,535 | B2 | 2/2011 | Cantin et al. |
| 7,883,536 | B1 | 2/2011 | Bendett et al. |
| 7,899,512 | B2 | 3/2011 | Labadie et al. |
| 7,908,010 | B2 | 3/2011 | Greenberg et al. |
| 7,909,867 | B2 | 3/2011 | Myung et al. |
| 7,914,842 | B1 | 3/2011 | Greenberg et al. |
| 7,951,181 | B2 | 5/2011 | Mahadevan-Jansen et al. |
| 7,988,688 | B2 | 8/2011 | Webb et al. |
| 8,012,189 | B1 | 9/2011 | Webb et al. |
| 2002/0002391 | A1 | 1/2002 | Gerdes |
| 2003/0236458 | A1 | 12/2003 | Hochman |
| 2004/0116980 | A1* | 6/2004 | Ohta et al. ............. 607/54 |
| 2004/0225339 | A1 | 11/2004 | Yaroslavsky et al. |
| 2004/0236421 | A1* | 11/2004 | Lipshitz et al. .......... 623/6.27 |
| 2005/0099824 | A1 | 5/2005 | Dowling et al. |
| 2005/0143789 | A1 | 6/2005 | Whitehurst et al. |
| 2006/0161218 | A1 | 7/2006 | Danilov |
| 2006/0167564 | A1 | 7/2006 | Flaherty et al. |
| 2006/0276861 | A1 | 12/2006 | Lin |
| 2007/0053996 | A1 | 3/2007 | Boyden et al. |
| 2007/0054319 | A1 | 3/2007 | Boyden et al. |
| 2007/0191906 | A1 | 8/2007 | Iyer et al. |
| 2007/0260297 | A1 | 11/2007 | Chariff |
| 2007/0261127 | A1 | 11/2007 | Boyden et al. |
| 2008/0009748 | A1 | 1/2008 | Gratton et al. |
| 2008/0077200 | A1 | 3/2008 | Bendett et al. |
| 2008/0086206 | A1 | 4/2008 | Nasiatka et al. |
| 2008/0161697 | A1 | 7/2008 | Chance |
| 2009/0030327 | A1 | 1/2009 | Chance |
| 2009/0054954 | A1 | 2/2009 | Foley et al. |
| 2009/0076115 | A1 | 3/2009 | Wharton et al. |
| 2009/0163982 | A1 | 6/2009 | deCharms |
| 2009/0177255 | A1 | 7/2009 | Merfeld |
| 2009/0210039 | A1 | 8/2009 | Boyden et al. |
| 2010/0049180 | A1 | 2/2010 | Wells et al. |
| 2010/0114190 | A1 | 5/2010 | Bendett et al. |
| 2010/0145418 | A1 | 6/2010 | Zhang et al. |
| 2010/0152846 | A1* | 6/2010 | Vaillant et al. ............ 623/6.11 |
| 2010/0162109 | A1 | 6/2010 | Chatterjee et al. |
| 2010/0184818 | A1 | 7/2010 | Wharton et al. |
| 2010/0292758 | A1 | 11/2010 | Lee et al. |
| 2011/0172725 | A1 | 7/2011 | Wells et al. |

OTHER PUBLICATIONS

Allegre, et al., "Stimulation in the rat of a nerve fiber bundle by a short UV pulse from an excimer laser", "NeuroScience Letters ", 1994, pp. 261-264, vol. 180.

Arridge, et al., "The theoretical basis for the determination of optical pathlengths in tissue: temporal and frequency analysis", "Phys. Med. Biol. ", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Bashkato, A., et al., "Optical Clearing of Human Eye Sclera", "Proc. of SPIE", 2009, pp. 71631R-1-71631R-8, vol. 7163.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience ", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science ", Oct. 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Haggard, "The Sources of Human Volition", "Science", May 8, 2009, pp. 731-733, vol. 324.

Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, p. e299, No. 3, Publisher: www.plosone.org.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008 , vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg. ", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , p. 064036, vol. 10, No. 6.

Princeton Lightwave (Company), "High Power Water Cooled Laser Stack", "http://www.princetonlightwave.com/content/pli_high_power_multimode_laser_stacks.pdf", (downloaded Dec. 2005.

Princeton Lightwave (Company), "High Power Single Element Laser", "www.princetonlightwave.com/content/HP%20Single%20Element%20Laser%20version%202.pdf", 2005.

(56) References Cited

OTHER PUBLICATIONS

Rolfe, "In Vivo Near-Infrared Spectroscopy", "Annu. Rev. Biomed. Eng.", 2000, pp. 715-754, vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics ", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", Jul. 23, 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al. , "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al. , "Channelrhodopsin-2 and optical control of excitable cells", "Nature Methods", Sep. 21, 2006, pp. 785-792, vol. 3, No. 10.

* cited by examiner

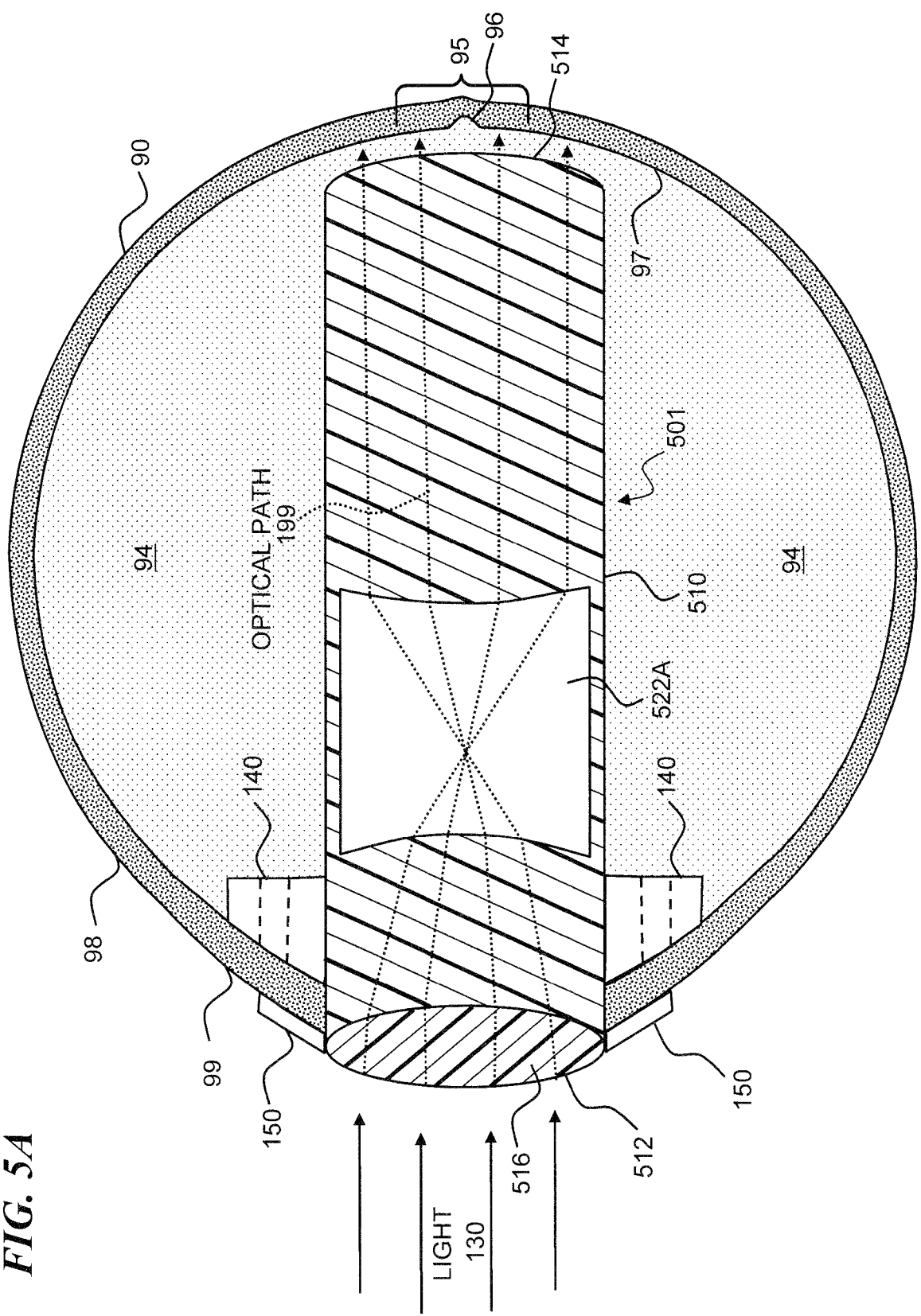

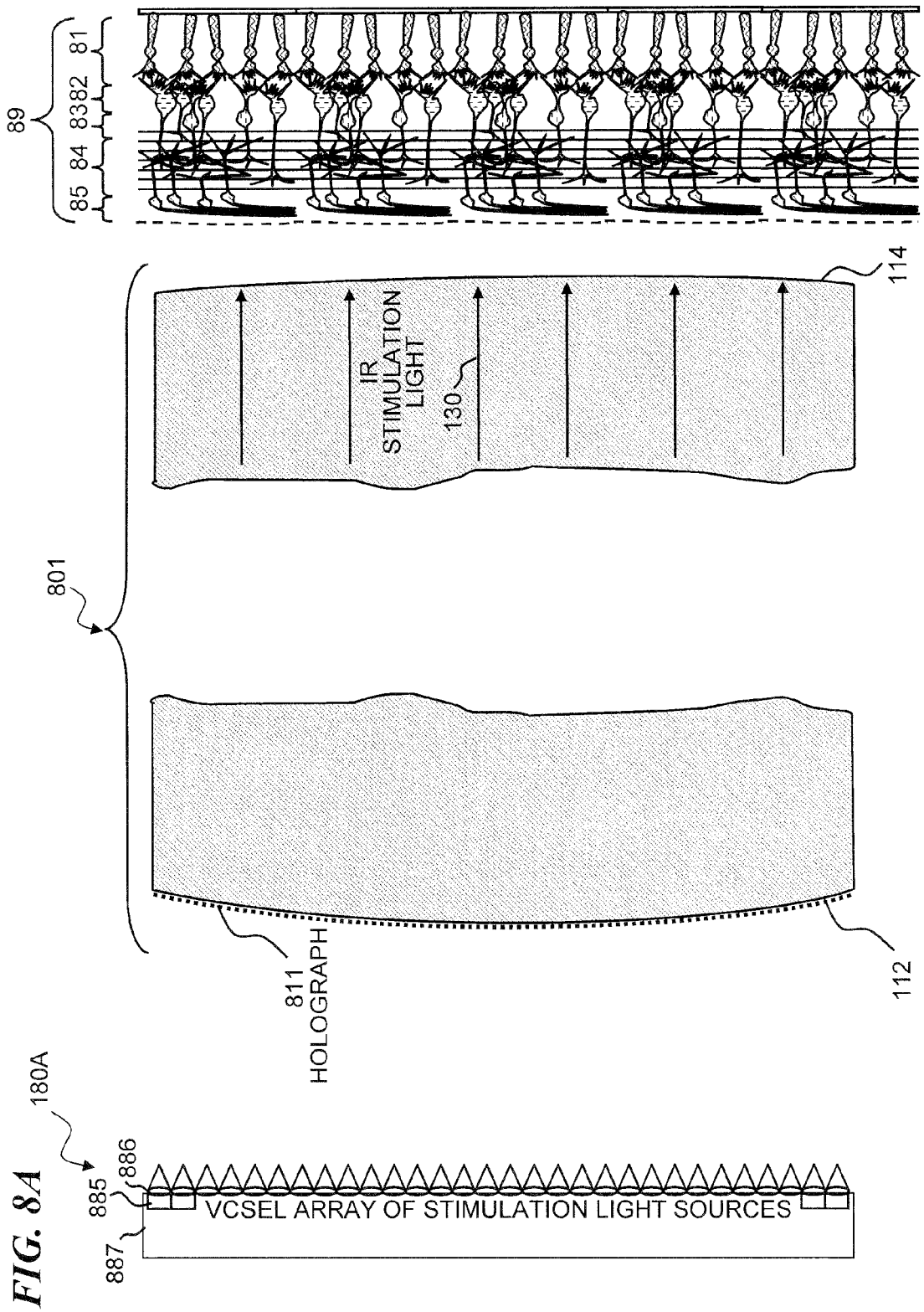

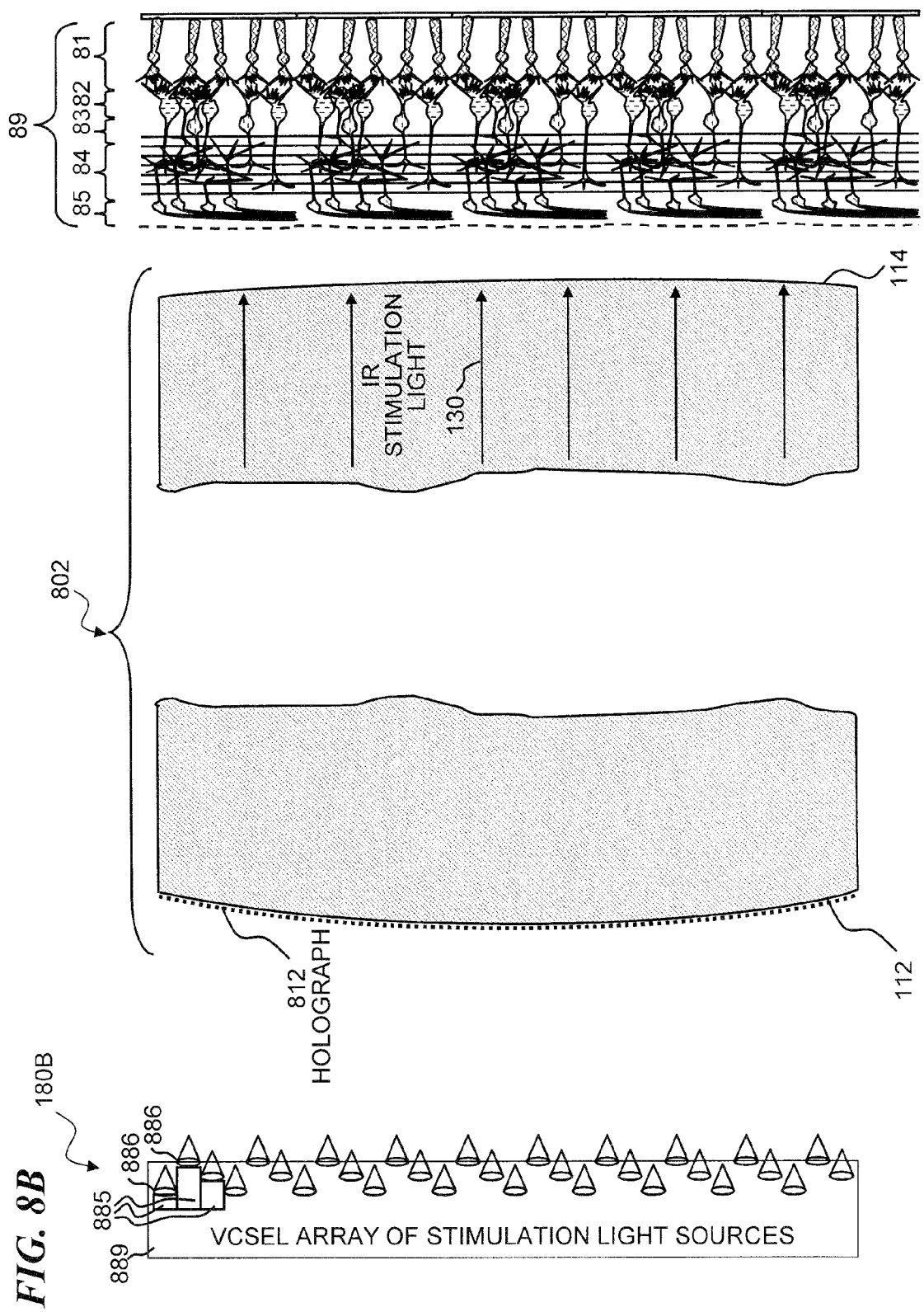

Transmittance of general purpose acrylic and two ultraviolet transmitting acrylics as a function of wavelength. Sample thickness = 1/8" (3.17 mm) nominal. (from www.fresneltech.com)

OCULAR IMPLANT WITH SUBSTANTIALLY CONSTANT RETINAL SPACING FOR TRANSMISSION OF NERVE-STIMULATION LIGHT

CROSS-REFERENCE TO RELATED APPLICATIONS

This application claims priority benefit under 35 U.S.C. §119(e) of U.S. Provisional Patent Application No. 61/514,894 filed Aug. 3, 2011, titled "Sight-Restoring Visual Prosthetic and Method Using Infrared Nerve-Stimulation Light", which is incorporated herein by reference in its entirety.

This invention is related to the following prior applications and patents:

U.S. Provisional Patent Application No. 60/715,884 filed Sep. 9, 2005, titled "Apparatus and Method for Optical Stimulation of Nerves";

U.S. patent application Ser. No. 11/257,793 filed Oct. 24, 2005, titled "Apparatus for Optical Stimulation of Nerves and Other Animal Tissue" (now U.S. Pat. No. 7,736,382 issued Jun. 15, 2010);

U.S. Provisional Patent Application No. 60/826,538 filed Sep. 21, 2006, titled "Miniature Apparatus and Method for Optical Stimulation of Nerves and Other Animal Tissue";

U.S. patent application Ser. No. 11/536,639 filed Sep. 28, 2006, titled "Miniature Apparatus and Method for Optical Stimulation of Nerves and Other Animal Tissue" (now U.S. Pat. No. 7,988,688 issued Aug. 2, 2011);

U.S. patent application Ser. No. 11/536,642 filed Sep. 28, 2006, titled "Apparatus and Method for Stimulation of Nerves and Automated Control of Surgical Instruments";

U.S. Provisional Patent Application No. 60/884,619 filed Jan. 11, 2007, titled "Vestibular Implant Using Infrared Nerve Stimulation";

U.S. patent application Ser. No. 11/971,874 filed Jan. 9, 2008, titled "Method and Vestibular Implant using Optical Stimulation of Nerves" (now U.S. Pat. No. 8,012,189 issued Sep. 6, 2011);

U.S. Provisional Patent Application No. 60/964,634 filed Aug. 13, 2007, titled "VCSEL Array Stimulator Apparatus and Method for Light Stimulation of Bodily Tissues";

U.S. patent application Ser. No. 12/191,301 filed Aug. 13, 2008, titled "VCSEL Array Stimulator Apparatus and Method for Light Stimulation of Bodily Tissues" (now U.S. Pat. No. 8,475,506 issued Jul. 2, 2013);

U.S. Provisional Patent Application No. 61/015,665 filed Dec. 20, 2007, titled "Laser Stimulation of the Auditory System at 1.94 μm and Microsecond Pulse Durations";

U.S. Provisional Patent Application No. 61/147,073 filed Jan. 23, 2009, titled "Optical Stimulation Using Infrared Lasers (or In Combination with Electrical Stimulation) of the Auditory Brainstem and/or Midbrain";

U.S. patent application Ser. No. 12/693,427 filed Jan. 25, 2010, titled "Optical Stimulation of the Brainstem and/or Midbrain, including Auditory Areas";

U.S. Provisional Patent Application No. 61/349,813 filed May 28, 2010, by Jonathon D. Wells et al., titled "Laser-Based Nerve Stimulators for, e.g., Hearing Restoration in Cochlear Prostheses";

U.S. Provisional Patent Application No. 61/381,933 filed Sep. 10, 2010, by Jonathon D. Wells et al., titled "Laser-Based Nerve Stimulators for, e.g., Hearing Restoration in Cochlear Prostheses and Method";

U.S. patent application Ser. No. 12/890,602 filed Sep. 24, 2010, by Jonathon D. Wells et al., titled "Laser-Based Nerve Stimulators for, e.g., Hearing Restoration in Cochlear Prostheses and Method";

U.S. Provisional Patent Application No. 61/349,810 filed May 28, 2010, by Jonathon D. Wells et al., titled "Implantable Infrared Nerve Stimulation Devices for Peripheral and Cranial Nerve Interfaces";

U.S. Provisional Patent Application No. 61/386,461 filed Sep. 24, 2010, by Jonathon D. Wells et al., titled "Implantable Infrared Nerve Stimulation Devices for Peripheral and Cranial Nerve Interfaces";

U.S. patent application Ser. No. 13/117,121 filed May 26, 2011, by Jonathon D. Wells et al., titled "Implantable Infrared Nerve Stimulation Devices for Peripheral and Cranial Nerve Interfaces";

U.S. patent application Ser. No. 13/117,122 filed May 26, 2011, by Jonathon D. Wells et al., titled "Cuff Apparatus and Method for Optical and/or Electrical Nerve Stimulation of Peripheral Nerves" (now U.S. Pat. No. 8,652,187 issued Feb. 18, 2014); Nerves";

U.S. patent application Ser. No. 13/117,125 filed May 26, 2011, by Jonathon D. Wells et al., titled "Nerve-Penetrating Apparatus and Method for Optical and/or Electrical Nerve Stimulation of Peripheral Nerves";

U.S. patent application Ser. No. 13/117,118 filed May 26, 2011, by Jonathon D. Wells et al., titled "Optical Bundle Apparatus and Method for Optical and/or Electrical Nerve Stimulation of Peripheral Nerves";

each of which is incorporated herein by reference in its entirety.

FIELD OF THE INVENTION

The invention relates generally to methods and apparatus for vision restoration and optical nerve stimulation, and more particularly to a method and apparatus for transmission of infrared optical stimulation to nerves (in contrast to the regular optical sensing rod and cone cells) in a human eye to obtain a sensation of vision.

BACKGROUND OF THE INVENTION

For many patients suffering from retinal degenerative diseases such as advanced or age-related macular degeneration (AMD) and retinitis pigmentosa (RP) there has been little hope for maintaining vision. Every year, 700,000 new cases of AMD in the U.S. are diagnosed and 10% of those patients will become legally blind. There are presently no cures for these debilitating diseases, and, at best, current treatments only slow the disease progression. The overall social and economic impact of AMD and RP is immense and the importance of treating blindness is profound as this is a problem of significant scope and breadth. There is an unmet need to treat this ailment by developing a visual prosthetic with a large number (e.g., thousands) of stimulation channels to realistically restore sight using infrared light to stimulate the retinal nerves. Advanced macular degeneration and retinitis pigmentosa are both diseases that degrade vision in patients and eventually will lead to blindness.

Researchers have artificially stimulated various parts of the human nervous system for many years as a way to restore lost or damaged neural function of various systems in the human body. Neuroprosthetic devices circumvent non-functioning physiological structures (hair cells in the ear, rods and cones in the eye) which would normally transduce an external stimulus (sound, light) into an action potential. Presently, there are numerous efforts underway to develop neuroprostheses to restore sight at various interventional anatomical locations: in the subretina, the epiretina, the optic nerve and in the visual cortex. These devices apply an electric current pulse to stimulate the neurons of the visual system which is inherently hindered by a lack of spatial selectivity. Electrical current spread leads to imprecise nerve stimulation and limits the ability of the neuroprosthesis to restore function. The limitation of spatial selectivity is based on fundamental physical principles of electrical stimulation. To date, after 20 years of development, electrical implants are just now hoping to make the jump to 64-channel systems from 16-channel systems. This is far less than the thousands of channels estimated to be needed for a good vision prosthetic. The technology is further limited by the fact that physical contact is required with tissue, which can lead to damage over time. Implantation of a complex powered device in very close proximity to sensitive neural tissue forms a significant drawback to this approach, making it impossible to update the technology without further risky surgeries.

There have been rudimentary attempts to stimulate the retinal nerves with electrical signals, which are being conducted by various groups globally. For example, the Argus™ II implantable device, by Second Sight Medical Products, Inc., 12744 San Fernando Road—Building 3, Sylmar, Calif. 91342, USA, which is intended to treat profoundly blind people suffering from degenerative diseases such as RP. The Second Sight Medical Products, Inc. Argus™ II system works by converting video images captured from a miniature camera, housed in the patient's glasses, into a series of small electrical pulses that are transmitted wirelessly to an epiretinal prosthesis array of electrodes implanted inside the eye on the retina. These pulses then stimulate the retina's remaining cells resulting in the corresponding perception of patterns of light in the brain. Patients supposedly learn to interpret these visual patterns thereby gaining some functional vision.

U.S. Pat. No. 7,079,900 issued Jul. 18, 2006, to Greenburg et al., titled "Electrode Array for Neural Stimulation," is incorporated herein by reference. Greenburg et al. describe a retinal color prosthesis to restore color vision by electrically stimulating undamaged retinal cells, which remain in patients with lost or degraded visual function. There are three main parts: one is external to the eye, the second part is internal to the eye, and the third part communicates between those two parts. The external part has color imaging means (CCD or CMOS video camera), an eye-tracker, a head-motion tracker, a data processor, a patient's controller, a physician's local controller, a physician's remote controller, and a telemetry means. The color data is processed in the video data processing unit and encoded by time sequences of pulses separated by varying amounts of time, and also with the pulse duration being varied in time. The basis for the color encoding is the individual color code reference. Direct color stimulation is another operational basis for providing color perception. The electrodes stimulate the target cells so as to create a color image for the patient, corresponding to the original image as seen by the video camera. The physician's test unit can be used to set up or evaluate and test the implant during or soon after implantation.

U.S. Pat. No. 7,914,842 issued Mar. 29, 2011, to Greenberg et al., titled "Method of Manufacturing a Flexible Circuit Electrode Array," is incorporated herein by reference. Greenberg et al. describe polymer materials and electrode array bodies for neural stimulation, especially for retinal stimulation to create vision. The method lays down a polymer layer, applies a metal layer to the polymer and pattern to create electrodes and leads, and applies a second polymer layer over the metal layer and pattern to leave openings for electrodes. The array and its supply cable are a single body.

Electrical stimulation represents a major challenge in developing implantable devices with long-term system performance while reducing their overall size. The Boston Retinal Implant Project has identified long-term biocompatibility as one of the most significant challenges to be met in order to develop a successful retinal prosthesis. For example, U.S. Pat. No. 6,324,429 issued Nov. 27, 2001, to Shire et al., titled "Chronically Implantable Retinal Prosthesis," is incorporated herein by reference. Shire et al. describe a chronically implantable retinal prosthesis for the blind which will restore some useful vision to patients over at least several degrees of their former field of view. These thin, strong, and flexible epiretinal devices are constructed of or encapsulated in known biocompatible materials which will have a long working life in the eye's saline environment. The function of the implants is to electrically stimulate the ganglion cell layer at the surface of the retina using controlled current sources. Due to the exceptionally low mass of the implant and its flexible, nearly planar form, patient discomfort and fluid drag caused by the implant minimized. These physical attributes also substantially reduce the potential of harm to the most delicate structure of the eye, the retina, and therefore enhance the long term safety and biocompatibility of the device. Since no micro-cables are required to be attached to the device, and its overall form and edges are rounded, the device is not expected to stress the retina during chronic implantation. A provision is also made for nutrients to reach the retinal cells underneath the device to assure their long-term health.

U.S. Pat. No. 7,908,010 issued Mar. 15, 2011, to Greenberg et al., titled "Retinal Prosthesis with Side Mounted Inductive Coil," is incorporated herein by reference. Greenberg et al. describe a retinal prosthesis with an inductive coil mounted to the side of the eye by means of a strap around the eye. This allows for close coupling to an external coil and movement of the entire implanted portion with movement of the eyeball.

Electrical stimulation, as described in the above devices and patents, is limited since the spread of electricity does not allow separate or independent stimulation of individual retinal nerve cells or even small-enough groups of nerve cells for sharp or clear vision. This electrical-stimulation technology is severely limited, as electricity spreads in human tissue and thus will severely limit the number of stimulation sites. Electrical stimulation thus greatly limits the number of sites that could be separately stimulated. Additionally, the electrical-stimulation approach will require implantation of a powered (e.g., an electrically powered) device, which has significant, difficult issues associated with obtaining power into the eye and using the power by devices in the eye.

Other work is being done in the area of optogenetics wherein a virus is used to genetically sensitize nerve cells to certain wavelengths of light, e.g., PCT publication WO 2010/011404 A2 titled "Vectors for Delivery of Light-Sensitive Proteins and Methods of Use," which is incorporated herein by reference. This area may have some potential, however it will require significant development work, it involves injecting a virus into nerve tissue (which may have significant side effects and FDA-approval issues), and the virus is only partially taken up by nerve cells.

Materials that are compatible with the eye are described in U.S. Pat. No. 6,254,637 to Jin Hak Lee et al., titled "Artificial Cornea and Implantation Thereof"; U.S. Pat. No. 6,391,055 to Yoshito Ikada et al., titled "Artificial Cornea"; U.S. Pat. No. 6,976,997 to Noolandi et al., titled "Artificial Cornea"; U.S. Pat. No. 7,857,849 to David Myung et al., titled "Artificial corneal implant"; and U.S. Pat. No. 7,909,867 to David Myung et al., titled "Interpenetrating Polymer Network Hydrogel Corneal Prosthesis"; each of which is incorporated herein by reference in its entirety.

Numerous digital light projection micro-electro-mechanical-system (MEMS) devices exist. For example, U.S. Pat. No. 4,566,935 issued to Hornbeck on Jan. 28, 1986, titled "Spatial Light Modulator and Method" and is incorporated herein by reference in its entirety. Hornbeck described methods of fabrication of spatial light modulators with deflectable beams by plasma etching after dicing of a substrate into chips, each of the chips an SLM. Various architectures available with such plasma etching process were disclosed and include metal cloverleafs for substrate addressing, metal flaps formed in a reflecting layer over a photoresist spacer layer, and torsion hinged flaps in a reflecting layer.

As another MEMS display example, U.S. Pat. No. 7,776,631 issued to Miles on Aug. 17, 2010, titled "MEMS Device and Method of Forming a MEMS Device," and is incorporated herein by reference in its entirety. Miles described light in the visible spectrum being modulated using an array of modulation elements, and control circuitry connected to the array for controlling each of the modulation elements independently, each of the modulation elements having a surface which is caused to exhibit a predetermined impedance characteristic to particular frequencies of light.

U.S. Pat. No. 7,177,081 issued to Tomita et al. on Feb. 13, 2007, titled "High Contrast Grating Light Valve Type Device," and is incorporated herein by reference in its entirety. Tomita et al. describe a grating light valve with a plurality of spaced reflective ribbons that are spatially arranged over a substrate with reflective surfaces. The grating light valve is configured to optimize the conditions for constructive and destructive interference with an incident light source having a wavelength $\lambda$. The grating light valve preferably has a set of movable active ribbons alternating between the set of stationary bias ribbons. In operation, active ribbons are moved by a multiple of $\lambda/4$ to switch between the conditions for constructive and destructive interference.

U.S. Pat. No. 4,720,189 issued Jan. 19, 1988 to Heynen et al., titled "Eye-Position Sensor," is incorporated herein by reference in its entirety. Heynen et al. describe an eye-position sensor for use in an eye-activated optical transducer in which a spatial filter is used to modify light reflected from the eye to form a substantially rectangular pattern on a quadrantal array of contiguous sensors. This arrangement provides a substantially linear change in the output signal from the sensors in response to an equivalent movement of the eye.

U.S. Pat. No. 6,055,110 issued Apr. 25, 2000, to Kintz et al., titled "Compact Display System Controlled by Eye Position Sensor System," is incorporated herein by reference in its entirety. Kintz et al. describe a virtual image display system is provided which is made thinner through the use of an immersed beam splitter, and in one embodiment, total internal reflection. The display system includes an imaging surface on which a source object is formed, a first optical element having a reflective function and a magnification function, a second optical element having a magnification function and an immersed beam splitting element positioned between the first and second optical elements, the immersed beam splitting element including a beam splitter surrounded by an optically transparent material having a refractive index greater than air. An illumination source projects the source object formed at the imaging surface through the optically transparent material to the beam splitter. The beam splitter reflects the projected source object to the first optical element. The first optical element magnifies the projected source object and reflects a magnified virtual image of the projected source object to the beam splitter. The magnified virtual image traverses the beam splitter to the second optical element which magnifies the magnified virtual image to produce a compound magnified virtual image of the source object.

There remains a need in the art for an improved prosthesis and method for stimulating vision nerves to obtain a vision sensation that is more useful for the patient.

BRIEF SUMMARY OF THE INVENTION

The present invention uses infrared nerve stimulation (INS) technology that uses infrared light to cause action potentials in nerve cells in the eye. In recent years, optical-stimulation technology has been developed to stimulate nerves. This INS technology can achieve much higher precision and selectivity of stimulation than using electrical current to trigger nerve action potentials. In some embodiments, the present technology uses pulsed, infrared lasers to excite the neural tissue next to the retina directly and without tissue damage. The advent of this technology represents a paradigm shift in artificial nerve stimulation because it allows a high degree of spatial selectivity of neural stimulation without the need for tissue contact.

The present invention provides an improved prosthesis and method for stimulating vision nerves to obtain a vision sensation that is useful for the patient that has lost vision due to AMD, RP, and other diseases. The invention utilizes infrared light to cause action potentials in the retinal nerves similar to those action potentials that result from rods and cones stimulated by visible light in healthy retinas. In a related invention by one of the inventors of the present invention, an eyeglass-mounted system is described that collects visual information and converts it into a stimulation pattern which is projected into the eye at an infrared wavelength with the purpose of causing an action potential in the retinal nerves with the purpose of recreating sight. As the infrared light stimulation wavelengths are normally strongly absorbed by the vitreous humor and tissues of the eye, in some embodiments the invention provides a pathway or "image pipe" for transmitting a stimulation pattern of infrared nerve-stimulation light, from an external infrared-light-emitting stimulator array, through the eye and focusing the stimulation pattern of infrared light on the nerves of the retina, especially the macula and fovea. In some embodiments, the invention provides improved resolution down to a group of nerves, or even the individual nerve level, with sufficient energy density so as to cause desired action potentials in the targeted nerves.

In some embodiments, a laser diode emitting light with a 1.87-micron wavelength stimulates nerves. This wavelength is important because devices capable of generating this wavelength are more available than longer mid-IR wavelengths. In some embodiments, laser-diode light of a 2.1-micron wavelength is used for nerve stimulation. Laser diodes that emit 2.1-micron-wavelength light are currently in research and would most likely work as well as other wavelengths, since this wavelength, when generated by a lamp-pumped solid-state laser, has been shown to be effective in stimulating nerves. In some embodiments, a laser-diode device (having one or more emitters) outputs light that is used for nerve stimulation, wherein the light has a wavelength of between about 1.5 microns and about 6 microns; in various embodiments, for example, the wavelength is in the far infrared at about 1.5 microns, or about 1.51 microns, about 1.52 microns, about 1.53 microns, about 1.54 microns, about 1.55 microns, about 1.56 microns, about 1.57 microns, about 1.58 microns, about 1.59 microns, about 1.6 microns, about 1.61 microns, about 1.62 microns, about 1.63 microns, about 1.64 microns, about 1.65 microns, about 1.66 microns, about 1.67 microns, about 1.68 microns, about 1.69 microns, about 1.7 microns, about 1.71 microns, about 1.72 microns, about 1.73 microns, about 1.74 microns, about 1.75 microns, about 1.76 microns, about 1.77 microns, about 1.78 microns, about 1.79 microns, about 1.8 microns, about 1.81 microns, about 1.82 microns, about 1.83 microns, about 1.84 microns, about 1.85 microns, about 1.86 microns, about 1.87 microns, about 1.88 microns, about 1.89 microns, about 1.9 microns, about 1.91 microns, about 1.92 microns, about 1.93 microns, about 1.94 microns, about 1.95 microns, about 1.96 microns, about 1.97 microns, about 1.98 microns, about 1.99 microns, about 2.0 microns, about 2.01 microns, about 2.02 microns, about 2.03 microns, about 2.04 microns, about 2.05 microns, about 2.06 microns, about 2.07 microns, about 2.08 microns, about 2.09 microns, about 2.1 microns, about 2.11 microns, about 2.12 microns, about 2.13 microns, about 2.14 microns, about 2.15 microns, about 2.16 microns, about 2.17 microns, about 2.18 microns, about 2.19 microns, about 2.2 microns, about 2.21 microns, about 2.22 microns, about 2.23 microns, about 2.24 microns, about 2.25 microns, about 2.26 microns, about 2.27 microns, about 2.28 microns, about 2.29 microns, about 2.3 microns, about 2.31 microns, about 2.32 microns, about 2.33 microns, about 2.34 microns, about 2.35 microns, about 2.36 microns, about 2.37 microns, about 2.38 microns, about 2.39 microns, about 2.4 microns, about 2.5 microns, about 2.6 microns, about 2.7 microns, about 2.8 microns, about 2.9 microns, about 3 microns, about 3.1 microns, about 3.2 microns, about 3.3 microns, about 3.4 microns, about 3.5 microns, about 3.6 microns, about 3.7 microns, about 3.8 microns, about 3.9 microns, about 4 microns, about 4.1 microns, about 4.2 microns, about 4.3 microns, about 4.4 microns, about 4.5 microns, about 4.6 microns, about 4.7 microns, about 4.8 microns, about 4.9 microns, about 5 microns, about 5.1 microns, about 5.2 microns, about 5.3 microns, about 5.4 microns, about 5.5 microns, about 5.6 microns, about 5.7 microns, about 5.8 microns, about 5.9 microns, or about 6.0 microns, or, in other embodiments, in ranges between any two of the above values. In other embodiments, an LED having output wavelengths centered in one of these ranges is used as a source of light to stimulate nerves.

In some embodiments, the implant includes a material which is both biocompatible in the eye and highly transmissive at the infrared stimulation wavelengths. In some embodiments, the implant includes optics that focus, collimate, and/or guide the stimulation light. In some embodiments, the implant is sewn, stapled, or otherwise secured at the sclera and/or sewn, stapled, or otherwise secured to those locations where the eye's natural lens is normally attached. In some embodiments, the implant is totally encapsulated within the eye, while in some other embodiments, the implant extends through the cornea and/or sclera. In some embodiments, the ocular implant uses materials and design features already used in artificial corneas and intraocular lenses, for example, such as described in U.S. Pat. No. 6,254,637 to Jin Hak Lee et al., titled "Artificial Cornea and Implantation Thereof"; U.S. Pat. No. 6,391,055 to Yoshito Ikada et al., titled "Artificial Cornea"; U.S. Pat. No. 6,976,997 to Noolandi et al., titled "Artificial Cornea"; U.S. Pat. No. 7,857,849 to David Myung et al., titled "Artificial corneal implant"; and U.S. Pat. No. 7,909,867 to David Myung et al., titled "Interpenetrating Polymer Network Hydrogel Corneal Prosthesis"; each of which is incorporated herein by reference in its entirety.

In some embodiments, once surgically implanted in the eye, the ocular implant has no internal moving parts relative to the eyeball and no internal electrical parts. Thus, such an ocular implant requires no internal or external electrical-power source. Additionally, the ocular implant does not impede movement of the eyeball after surgical implantation. In some embodiments, the freedom of eye movement relative to the external stimulator light can help provide enhanced patient comfort and enhanced perceived image resolution.

In some embodiments, the present invention provides a VCSEL array configured to output light pulses capable of optically stimulating neural tissue (e.g., cochlear nerve tissue, deep brain tissue, white brain matter tissue, gray brain matter tissue, spinal cord tissue, cardial nerve tissue, central nervous system nerve tissue, olfactory nerve tissue, optic nerve tissue, nerve bundles and the like). In some embodiments, the stimulating lights pulses have a wavelength that results in the appropriate penetration depth for effective stimulation of the tissue of interest without causing tissue damage (e.g., in some embodiments, the wavelength of stimulating light pulses is in the range of about 1.8 microns to about 2.2 microns, in some embodiments, the wavelength of stimulating light pulses is in the range of about 1.85 microns to about 2.0 microns, in some embodiments, the wavelength of stimulating light pulses is about 1.87 microns, in some other embodiments the wavelength of stimulating light pulses is in the range of about 4.0 microns to about 5.0 microns, in some other embodiments the wavelength of stimulating light pulses is in the range of about 4.2 microns to about 4.8 microns, in some other embodiments the wavelength of stimulating light pulses is in the range of about 4.4 microns to about 4.6 microns).

BRIEF DESCRIPTION OF THE DRAWINGS

FIG. 5A is a side cross-section view of an eye 90 that illustrates an implanted ocular unit 501 according to some embodiments of the invention.

FIG. 8A is a side cross-section view of a stimulation system 801 that uses a single-depth VCSEL array 887 and a holographic imager 811.

FIG. 8B is a side cross-section view of a stimulation system 802 that uses a VCSEL array 888 having a plurality of depths and a holographic imager 812.

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1A:
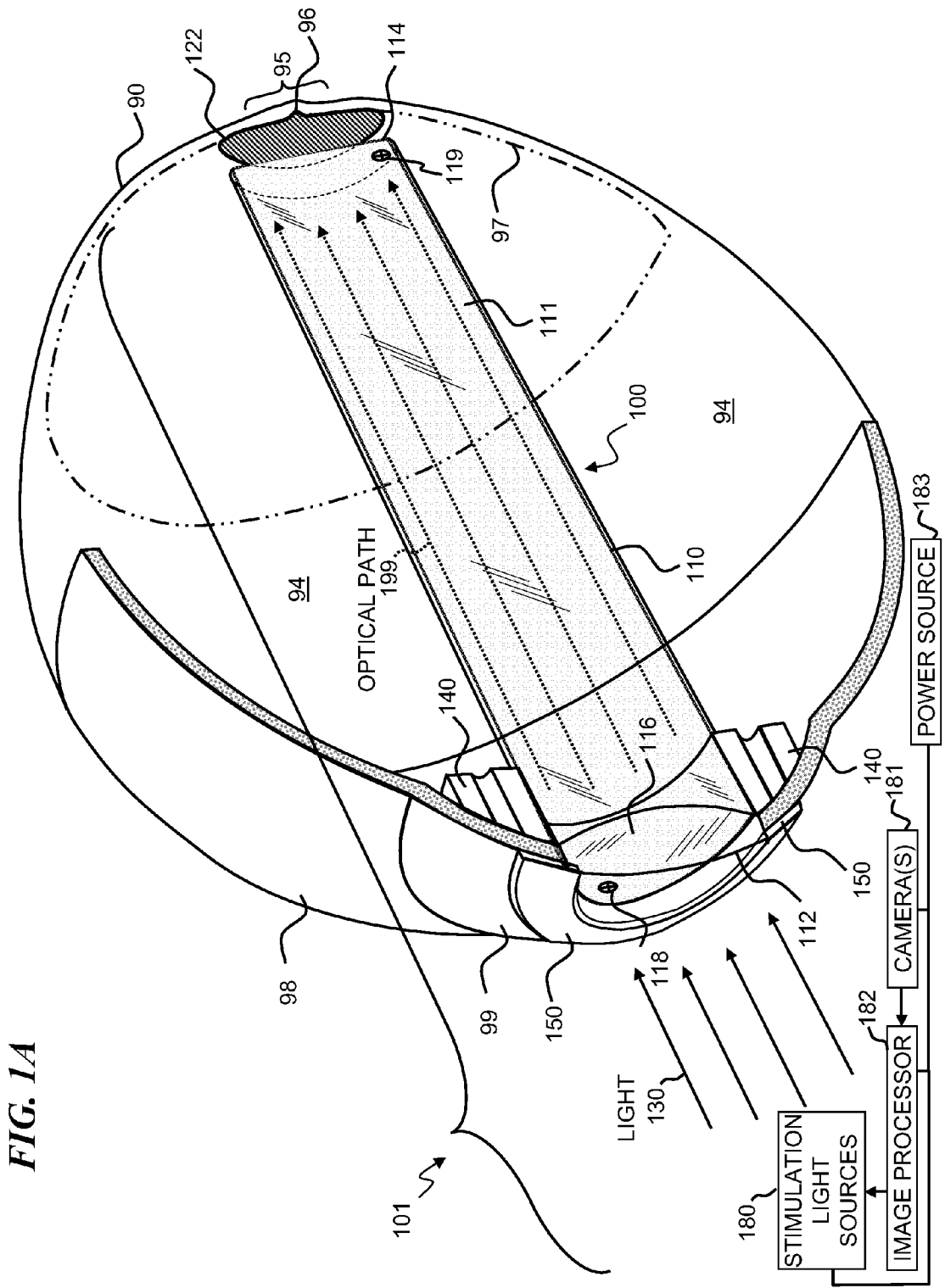
FIG. 1A is a cut-away perspective view of an eye 90 that illustrates an implanted ocular unit 100 according to some embodiments of the invention.

FIG. 1A is a cut-away perspective view of a nerve-stimulation system 101 for an eye 90 that illustrates an implanted ocular unit 100, according to some embodiments of the invention. In some embodiments, the ocular unit 100 includes a light-transparent pathway or "image pipe" 110 (which includes an optional lens system 116 and a transparent body 111) for transmitting a stimulation pattern of infrared light 130 from an external stimulator array 180 through the eye 90 along optical path 199, the ocular unit 100 having a light-receiving anterior end 112 closest to the eye's anterior surface and extending to a posterior end 114 of image pipe 110 closer to the fovea 96 than to the eye's anterior surface, transmitting light and/or projecting image 122 onto the retina 97, including onto the macula 95 and fovea 96. In some embodiments, the curved anterior surface of image pipe 110 acts as the anterior-end focussing element and no separately formed lens 116 is needed.

As used herein, an "image pipe" is an optical device that forms an image just beyond its posterior end (e.g., when an image pipe of the present invention is implanted in the eye, the image is formed on the nerves at the anterior surface of the retina) that is based on light 130 entering the anterior end. In some embodiments, an image pipe includes internal imaging components such as lenses, holographs, fiber optics or fiber-optic bundles, or the like, which assist in providing a focussed image at the retina. In other embodiments, the image pipe is simply a transparent path that allows external imaging components to form the image on the nerves at the front surface of the retina. Because some embodiments of the present invention use single-wavelength infrared lasers, holographic imagers are well suited to form images through such an image pipe.

In some embodiments, the image pipe 110 is substantially transparent to at least some infrared wavelengths of light between about 1000 nm and about 2000 nm, and in particular, is substantially transparent to those infrared wavelengths output by the source lasers of the stimulation apparatus. In some embodiments, the image pipe 110 has a substantially cylindrical shape such as shown in FIG. 1A, such that both ends of the image pipe 110 have substantially the same diameter. In some embodiments, the image pipe 110 is formed from a biocompatible-transparent-thermoplastic material such as poly(methyl methacrylate) (PMMA), or the like. In some embodiments, such as shown in FIG. 1A, the light-receiving anterior end 112 of ocular unit 100 replaces at least a portion of the cornea 99 of the eye and thus forms part of the anterior surface of the eye.

Poly(methyl methacrylate) (PMMA) is a transparent thermoplastic. PMMA has been sold under many different names including Plexiglas®, Lucite® and Perspex®. PMMA is substantially transparent (i.e., a given thickness of about a centimeter or more passes a majority of incident light) to visible light (having wavelengths of 400 nm to 700 nm) and infrared light (IR) having wavelengths from about 700 nm to about 2800 nm. Colored or tinted PMMA varieties allow specific IR wavelengths to pass while blocking visible light and/or other IR wavelengths.

In some embodiments, ocular unit 100 is surgically secured in place to the cornea 99 and/or sclera 98 in the eye with anchoring collar 140 and hydrogel skirt 150. In some embodiments, the implant is sewn (or stapled or otherwise anchored) to the ciliary muscle or secured to other internal parts of the eye to hold it securely in place. Ocular unit 100 extends well into the vitreous humor 94, which is less transparent than is image pipe 110 to certain infrared light wavelengths useful for nerve stimulation.

The posterior end 114 of the image pipe 110 is closer to the fovea than the front of the eye. In some embodiments, image pipe 110 has a length such that the posterior end 114 of the image pipe 110 is near the retina 97 in the region of the macula 95 and fovea 96. In some embodiments, the image pipe 110 does not contact the retina 97, in order to leave a pathway for the vitreous humor 94 to circulate and nourish the cells of the retina. In some embodiments, the posterior end 114 is positioned close enough to the retina 97 and fovea 96 such that the remaining vitreous humor is thin enough and transparent enough that infrared light output from the posterior end of the image pipe 110 will be sufficiently intense to cause retinal-nerve stimulation (i.e., triggering of nerve action potentials in the nerves of the retina due to impinging pulses of infrared light).

In some embodiments, the ocular image pipe 110 is solid material. PMMA has a higher density than the vitreous humor. To more closely match the density of the vitreous humor, some embodiments of image pipe 110 include at least one hollow portion such that the overall density of the image pipe 110 is the same as the density of the surrounding vitreous humor and the center of mass of the image pipe 110 coincides with the center of rotation of the eye, in order that the image pipe 110 does not tend to move relative to the eye with movement. In some embodiments, the hollow portion is filled with an inert gas. In some embodiments, the hollow portion is filled with a low-pressure gas having a pressure of no more than about 1000 Torr. In some embodiments, the hollow portion is in the light path of the light path and at least one end of the hollow portion is shaped to form a lens to focus the infrared light on nerves of the retina.

The placement, size, and shape of the hollow portion in the image pipe 110 is used in some embodiments to not only match the density of the vitreous humor but to also control the center of gravity to help provide a more stable implant the is resistant to movement of the head or eyeball. In some embodiments, the light-transmitting portion of image pipe 110 is solid material and the hollow portion is formed in a peripheral portion outside and surrounding the light-transmitting path. This configuration reduces the number of optical interfaces in the light path. In some embodiments, the light-transmitting portion of image pipe 110 is solid material and the hollow portion is formed symmetrically around a peripheral portion outside and surrounding the light-transmitting path, such that regardless of whether the person's head is upright or is lying on one side, there is no rotational or other force acting to move the implant (i.e., image pipe 110) relative to the eye. In other embodiments, the hollow portion is formed in (or is very slightly larger in) a top portion of image pipe 110, in order to help keep the image pipe 110 upright and in the desired position when the patient's head is upright.

In some embodiments, one or both ends of the image pipe 110 are shaped to focus the external stimulator light signals 130 on the retina and fovea. In some embodiments, there is an external light source 180 that emits IR-wavelength stimulation light 130. For example, in some embodiments, source 180 includes a two-dimensional array of vertical-cavity surface-emitting lasers (VCSEL-array) that form an IR stimulator, which provides IR light 130 into the anterior end 112 of the ocular implant 100. In some embodiments, the user has an ocular unit 100 implanted in each eye, and the system provides there is a separate external two-dimensional array IR stimulator source 180 for each eye, wherein the two separate images help provide three-dimensional images to the brain through each eye's ocular unit 100. In some embodiments, image pipe 110 includes a lens or lens system 116, with a different index of refraction than the rest of image pipe 110, to focus the image on the retina 97. In some embodiments, the lens system 116 inverts the incoming image and focuses the image on the retina. In some other embodiments, the lens system 116 is noninverting and directs diverging, collimated, or converging light on the nerve-tissue layer of the retina 97. In some embodiments, the image pipe 110 and its lens 116, in combination with an external laser image-generation device 180 and its image processor(s) 182 and one or more cameras in camera system 181, produce an infrared image on the retina, similar to the inverted optical-wavelength image a normal human eye. Since the human brain will automatically accustom itself to any image consistently formed on the retina whether or not the image is inverted, the camera system 181, image processor 182 and stimulation light sources 180 can be configured to form the image as inverted or not according to the preferences of the user. In some embodiments, camera system 181 includes at least one camera directed toward the user's eye (e.g., to determine the locations of indicia 118 and/or 119) to determine the location and/or direction of movement of the gaze of the user, and this image of the eye (or of the indicia 118/119) is processed by image processor system 182 in order to control the position of the stimulation light sources that are generating the stimulation light signals 130, in order to position the projected pattern of stimulation light onto the desired locations on retina 122. In some embodiments, the array of light sources 180 themselves are physically moved to the desired position based on a detection of the position of the eye (e.g., a flat VCSEL array mounted on a gimbal and rotated on one or more axes by servos that are controlled by signals based on the detected eye position), while in other embodiments, different ones of the light sources 180 that are already in the desired positions relative to the eye are activated. In some embodiments, eye-position sensors (such as described in U.S. Pat. No. 4,720,189 issued to Heynen et al. on Jan. 19, 1988, titled "Eye-Position Sensor," and U.S. Pat. No. 6,055,110 issued to Kintz et al. on Apr. 25, 2000, titled "Compact Display System Controlled by Eye Position Sensor System," which are each incorporated herein by reference in its entirety) detect a position of the eye (e.g., the direction to which the eye is pointing and/or the distance between the eye and the stimulation-light projector 180) and provide signals to a display positioning device (such as servo-controlled gimbals) that then moves one or more components of the stimulation-light projector 180 in order to maintain a reference position of the display in a substantially constant spatial relationship to the eye, and/or adjusts a focussing element to maintain a focus of the IR-stimulation-light signals from stimulation-light projector 180 onto the desired nerve layer of the retina. In some embodiments, a power source 183 is operatively coupled to supply power to operate the camera system 181, the image processor system 182, and the stimulation light sources 180.

In other embodiments, one or more grating light valves (such as described in U.S. Pat. No. 7,177,081 titled "High Contrast Grating Light Valve Type Device," which is incorporated herein by reference in its entirety) and/or one or more digital light projector devices (such as described in U.S. Pat. No. 4,566,935 issued to Hornbeck on Jan. 28, 1986, titled "Spatial Light Modulator and Method," or U.S. Pat. No. 7,776,631 titled "MEMS Device and Method of Forming a MEMS Device," which are each incorporated herein by reference in its entirety) are used to modulate and/or direct light (e.g., from one or more lasers, LEDs or other suitable light-source devices) to desired locations.

In some embodiments, the ocular unit 100 has at least one indicia mark to facilitate detection of the eye's position. In some embodiments, the ocular unit has at least one indicia mark 118 on the anterior end to facilitate external detection of the position of the eye and the pointing directions. In some embodiments, the ocular unit 100 has at least one indicia mark 119 on the posterior end to facilitate external detection of the position of the eye and the pointing directions. In some embodiments, one or more indicia marks are placed on both the anterior end posterior end, and/or on one or more other locations on the ocular unit 100. In some embodiments the location and/or orientation of the implant is determined, for example, by obtaining an image of, or detecting reflected or fluorescent light from, the indicia mark or marks 118 and/or 119 and the external stimulator array signals are adjusted to compensate for the position of the eye (e.g., the image or pattern is moved such that the desired nerve tissue continues to be stimulated). In some such embodiments, an eye-position processor in the external image processor 182 uses an "inward-pointing" camera in camera system 181 (i.e., a camera pointed toward the user to obtain an image of the eye and/or indicia 118/119) to detect movement or position of the user's eye(s), and generates control signals that direct an external camera view (i.e., the direction in which the camera system 181 is pointing, or if a very-wide-angle lens and/or multiple cameras are used, which of the images obtained by camera system 181 is used), providing a more realistic sensation of "looking around" to the user, instead of requiring movement of the user's entire head to obtain different images. In some embodiments, a plurality of "outward-pointing" cameras is included in camera system 181 (i.e., a plurality of cameras pointed toward different directions in the environment surrounding user to obtain a plurality of images from which to select based on the detected direction of the user's gaze).

Figure 1B:
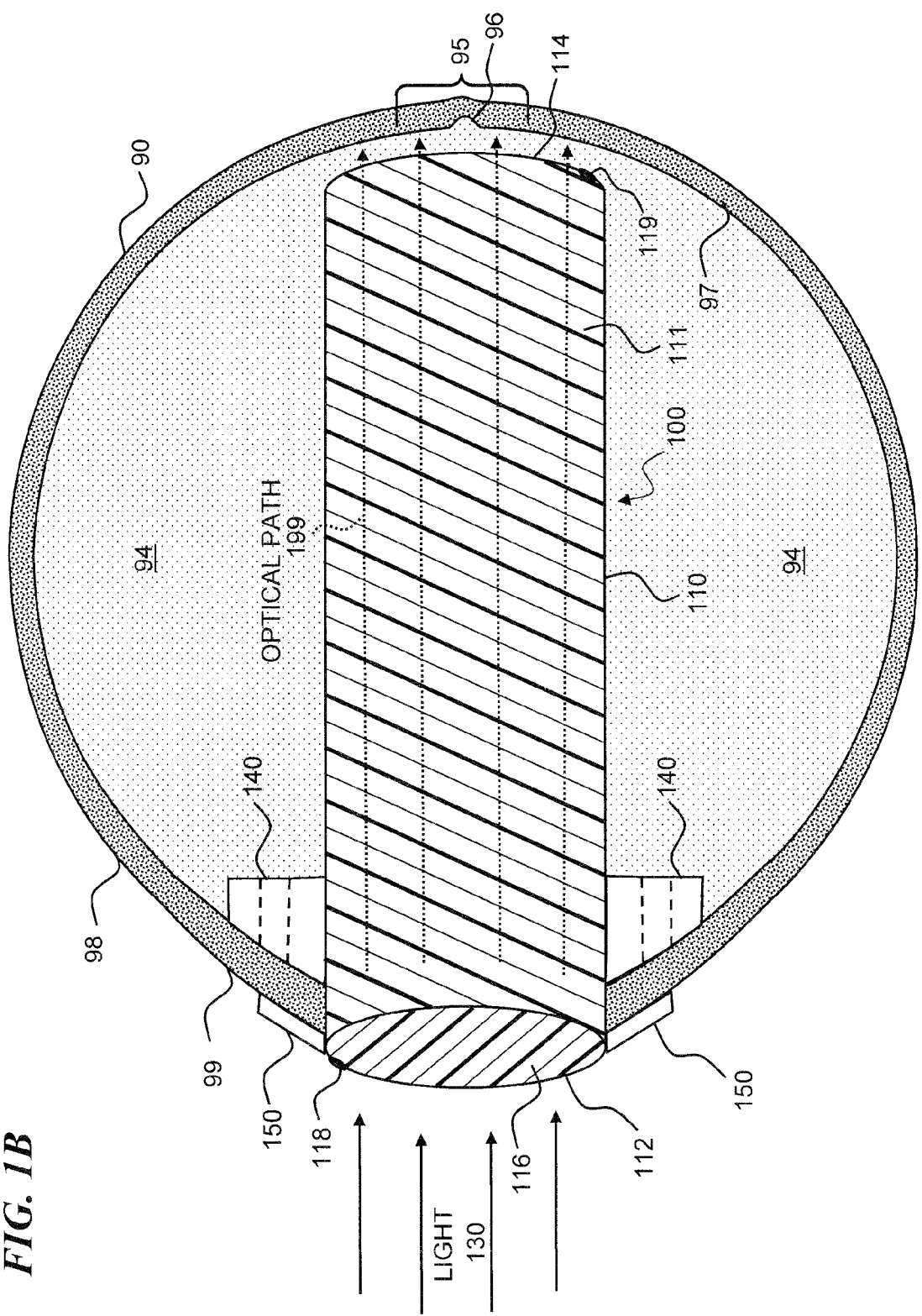
FIG. 1B is a side cross-section view of an eye 90 that illustrates an implanted ocular unit 100, similar to FIG. 1A, according to some embodiments of the invention.

FIG. 1B is a side cross-section view of an eye 90 that illustrates the implanted ocular unit 100, which is also shown in FIG. 1A, according to some embodiments of the invention. In some embodiments, the ocular unit 100 includes a light-transparent pathway or "image pipe" 110 for transmitting a stimulation pattern of infrared light from an external stimulator array through the eye, and a fastening mechanism (e.g., anchoring collar 140 and hydrogel skirt 150) for attaching the ocular unit 100 to the eye 90. The image pipe 110 has a light-receiving anterior end 112 closest to the eye's anterior surface and extending to a posterior end 114 of image pipe 110 closer to the fovea 96 than to the eye's anterior surface.

In some embodiments of ocular unit 100 of FIGS. 1A and 1B the posterior end 114 of image pipe 110 (and in some embodiments of the ocular units of FIGS. 2A, 2B, 3, 4, 5, and 6, the respective posterior ends of their image pipes) is within about 10 mm of the retina. In some embodiments, the posterior end of the image pipe is within about 8 mm of the retina. In some embodiments, the posterior end of the image pipe is within about 5 mm of the retina. In some embodiments, the posterior end of the image pipe is within about 4 mm of the retina. In some embodiments, the posterior end of image the pipe is within about 3 mm of the retina. In some embodiments, the posterior end of image the pipe is within about 2 mm of the retina. In some embodiments, the posterior end of image the pipe is within about 1 mm of the retina. In some embodiments, the posterior end of image the pipe is between about 1 cm and about 5 mm of the retina. In some embodiments, the posterior end of the image pipe is between about 5 mm and about 2 mm of the retina. In some embodiments of the ocular units of FIGS. 1A, 1B, 2A, 2B, 3, 4, 5, and 6, the light path within the ocular unit is at least 50% of the total distance from the anterior surface of the eye to the retina. In some embodiments of the ocular units of FIGS. 1A, 1B, 2A, 2B, 3, 4, 5, and 6, the light path within the ocular unit is at least 70% of the total distance from the anterior surface of the eye to the retina. In some embodiments of the ocular units of FIGS. 1A, 1B, 2A, 2B, 3, 4, 5, and 6, the light path within the ocular unit is at least 80% of the total distance from the anterior surface of the eye to the retina. In some embodiments of the ocular units of FIGS. 1A, 1B, 2A, 2B, 3, 4, 5, and 6, the light path within the ocular unit is at least 90% of the total distance from the anterior surface of the eye to the retina. In some embodiments of the ocular units of FIGS. 1A, 1B, 2A, 2B, 3, 4, 5, and 6, the light path within the ocular unit is at least 95% of the total distance from the anterior surface of the eye to the retina.

Note that in some embodiments, it is the entire system including exterior optics in the stimulation light source 180, along with the lens system 116 and body 110 of ocular unit 100 that act together to focus the image onto the desired nerve-tissue layer of the retina 97.

Figure 2A:
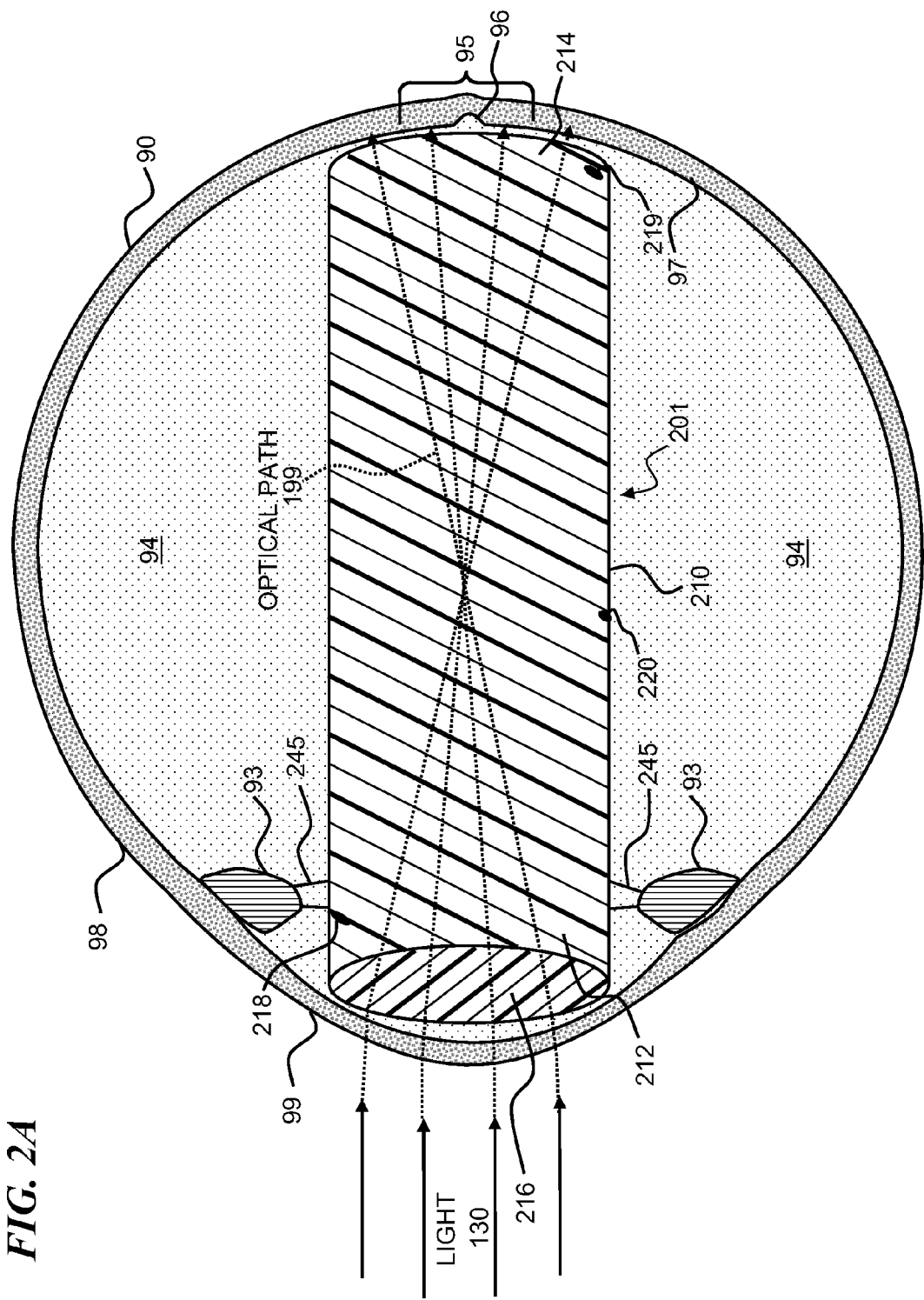
FIG. 2A is a side cross-section view of an eye 90 that illustrates an implanted intraocular unit 201 according to some embodiments of the invention.

FIG. 2A is a side cross-section view of an eye 90 that illustrates an implanted intra-ocular unit 201 according to some embodiments of the invention. In some embodiments, ocular unit 201 is similar to ocular unit 100 except ocular unit 201 is fully contained intraocularly (i.e., completely inside the eye) after being surgically implanted. In this embodiment, the image pipe 210 is surgically secured in place in the eye with the implant sewn, stapled, or otherwise secured 245 to the ciliary muscle 93 or secured to other internal parts of the eye to hold it securely in place. In some such embodiments, the ocular unit 201 is completely contained within the eye and the user's cornea 99 is maintained intact.

In some embodiments, the ocular unit 201 includes an image pipe 210 for transmitting a stimulation pattern of infrared light from an external stimulator array through the eye, the ocular unit 201 having a light-receiving anterior end 212 closest to the eye's anterior surface (behind the cornea) and extending to a posterior end 214 that is closer to the fovea than to the eye's anterior surface.

In some embodiments, the image pipe 210 is substantially transparent to at least some infrared wavelengths of light between about 1000 nm and about 2000 nm. In some embodiments, the image pipe 210 is substantially cylindrical-shaped such as shown in FIG. 2, such that both ends of the image pipe 210 have substantially the same diameter. In some embodiments, the image pipe 210 is formed from a biocompatible-transparent-thermoplastic material such as poly(methyl methacrylate) (PMMA), or the like.

The posterior end 214 of the image pipe 210 is closer to the fovea than the front of the eye. In some embodiments, image pipe 210 has a length such that the posterior end 214 of the image pipe 210 is near the retina 97 in the region of the fovea 96. In some embodiments, the image pipe 210 does not contact the retina, in order to leave a pathway for the vitreous humor of the eye to circulate and nourish the cells of the retina. In some embodiments, the posterior end 214 is positioned close enough to the retina 97 and fovea 96 such that the remaining vitreous humor 94 is thin enough and transparent enough that infrared light output from the posterior end of the image pipe 210 will be sufficiently intense to cause retinal-nerve stimulation (i.e., triggering of nerve action potentials in the nerves of the retina due to impinging pulses of infrared light).

In some embodiments, the ocular image pipe 210 is solid material. PMMA has a higher density than the vitreous humor. To more closely match the density of the vitreous humor, some embodiments of image pipe 210 include at least one hollow portion such that the overall density of the image pipe 210 is the same as the density of the surrounding vitreous humor and the center of mass of the image pipe coincides with the center of rotation of the eye, in order that the image pipe 210 does not tend to move relative to the eye with movement. In some embodiments, the hollow portion is filled with an inert gas. In some embodiments, the hollow portion is filled with a low-pressure gas having a pressure of no more than about 1000 Torr. In some embodiments, the hollow portion is in the light path of the light path and at least one end of the hollow portion is shaped to form a lens to focus the infrared light on nerves of the retina.

The placement, size, and shape of the hollow portion in the image pipe 210 is used in some embodiments to not only match the density of the vitreous humor but to also control the center of gravity to help provide a more stable implant the is resistant to movement of the head or eyeball. In some embodiments, the light-transmitting portion of image pipe 210 is solid material and the hollow portion is formed in a peripheral portion outside and surrounding the light-transmitting path. This configuration reduces the number of optical interfaces in the light path. In some embodiments, the light-transmitting portion of image pipe 210 is solid material and the hollow portion is formed symmetrically around a peripheral portion outside and surrounding the light-transmitting path, such that regardless of whether the person's head is upright or is lying on one side, there is no rotational or other force acting to move the implant (i.e., image pipe 210) relative to the eye. In other embodiments, the hollow portion is formed in (or is very slightly larger in) a top portion of image pipe 210, in order to help keep the image pipe 210 upright and in the desired position when the patient's head is upright.

In some embodiments, one or both ends of the image pipe 210 are shaped to focus the externally generated stimulator-array signals on the retina and fovea. In some embodiments, the present invention includes an external two-dimensional array VCSEL-array IR stimulator providing IR light 130 into the anterior end of the ocular implant 201.

In other embodiments of any of the embodiments of the present invention including the system described in FIG. 1A or FIG. 8A, other IR light sources are used, such as LED array emitters, or one or more single IR light sources that project light to an array modulator such as one or more grating light valves (for example, as described in U.S. Pat. No. 7,177,081 titled "High Contrast Grating Light Valve Type Device," which is incorporated herein by reference in its entirety) and/or one or more digital light projector devices (such as described in U.S. Pat. No. 4,566,935 issued to Hornbeck on Jan. 28, 1986, titled "Spatial light modulator and method," or U.S. Pat. No. 7,776,631 titled "MEMS Device and Method of Forming a MEMS Device," which are each incorporated herein by reference in its entirety), wherein the array light modulator provides a modulated nerve-stimulation signal to each of a plurality of locations on the patient's retina via the ocular implant 201. In yet other embodiments, any other suitable sources of IR stimulation light are used, including light sources emitting from a plurality of heights from their substrates (such as LED arrays or MEMS mirrors configured to focus at a plurality of depths in the nerves of the retina, such as shown in FIG. 8B).

In some embodiments, there is an external two-dimensional array IR stimulator for each eye to help provide three-dimensional images to the user with an ocular unit 201 implanted in each eye. In some embodiments, image pipe 210 includes a lens 216, with a different index of refraction than the rest of image pipe 210, to focus the image on the retina 97. In some embodiments, the lens 216 is a convex lens that has a higher index of refraction than the surrounding tissue and/or the body 210 of ocular unit 201 (or is a concave lens that has a lower index of refraction) and lens 216 (along with any external lens(es) and the cornea 99) inverts the incoming image and focuses the image on the retina. Note that in some embodiments, it is the entire system including exterior optics in the light source 180 and the cornea of the eye, along with the lens system 216 that act together to focus the image onto the desired nerve tissue. In some other embodiments, on the lens is noninverting and directs collimated light on the retina. In some embodiments, the image pipe 210, lens 216, in combination with an external laser-signal generation device produce an inverted nerve-stimulation pattern on the retina, similar to the inverted image a normal human eye.

In some embodiments, the ocular unit 201 has at least one indicia mark 218, 219, and/or 220 to facilitate detection of the eye's position. In some embodiments, the ocular unit has at least one anterior indicia mark 118, posterior indicia mark 119, or both to facilitate external detection of the position of the eye and the pointing direction of the gaze used for controlling the camera system 181 (e.g., moving the position/direction of the camera 181, or shifting the portion of the image obtained from the camera 181 and used to generation the stimulation signals 130). In some embodiments, indicia marks are placed on one or more other locations on the ocular unit 100. In some embodiments, reflected light from the indicia mark or marks is detected and the external stimulator array signals are adjusted to compensate for the position of the eye.

Figure 2B:
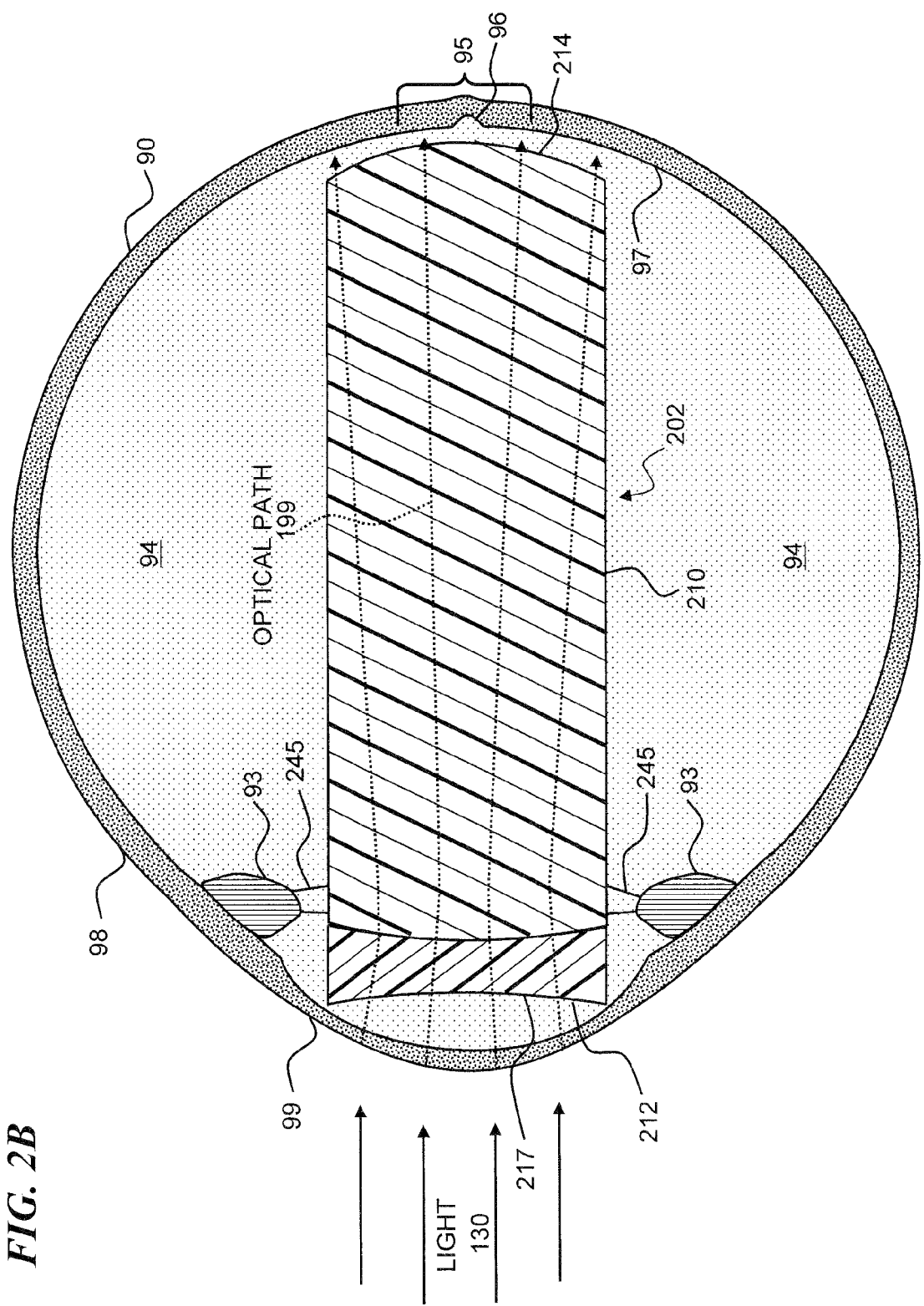
FIG. 2B is a side cross-section view of an eye 90 that illustrates an implanted intraocular unit 202 according to some embodiments of the invention.

FIG. 2B is a side cross-section view of an eye 90 that illustrates an implanted intra-ocular unit 202 according to some embodiments of the invention. In some embodiments, the lens 217 is a concave lens that has a higher index of refraction than the surrounding tissue and/or the body 210 of ocular unit 201 (or is a convex lens that has a lower index of refraction) and does not invert the incoming image in order to project the image on the nerves in the anterior surface of the retina. Note that in some embodiments, it is the entire system including exterior optics in the light source 180 and the cornea of the eye, along with the lens system 217 that act together to focus the image onto the desired nerve tissue.

Figure 2C:
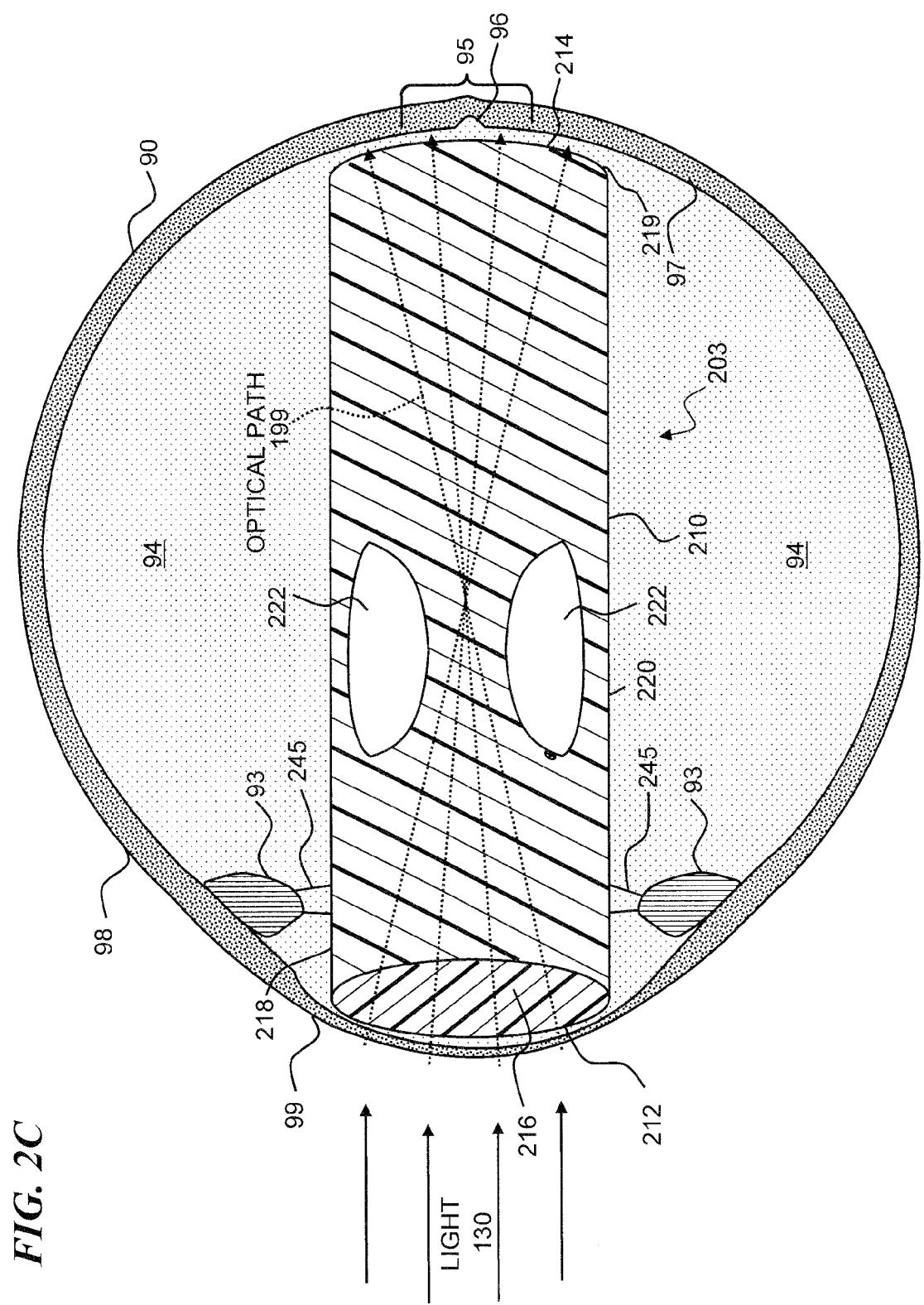
FIG. 2C is a side cross-section view of an eye 90 that illustrates an implanted intra-ocular unit 203 according to some embodiments of the invention.

FIG. 2C is a side cross-section view of an eye 90 that illustrates an implanted intra-ocular unit 203 according to some embodiments of the invention. In some embodiments, ocular unit 203 is identical to ocular unit 201 of FIG. 2A, except for including one or more bubbles or air-filled pockets 222, located outside of the optical path 199 (e.g., in some embodiments, along side of the focal point of the light focussed by lens 216) and used to provide a neutral buoyancy to ocular unit 203, so it neither floats toward the top of the eye 90, nor sinks toward the bottom of the eye 90, nor twists (e.g., up in back and down in front due to the different material densities of the lens 216 and body 210). In some embodiments, pockets 222 are coated with an opaque material, in order that they serve as an aperture or spatial filter, blocking light that is not part of the focussed stimulation-light image. In some embodiments, pockets 222 have one or more indicia 220 located such that an external camera can image the indicia and then determine the position of the eye 90, but also located off to the side of the optical path 199 such that the indicia do not interfere with or block any portion of the projected image of the stimulation light. In some embodiments, pockets 222 are formed of two or more separate bubbles located so as to provide a center of gravity point and neutral buoyancy to minimize unwanted movement of the ocular unit 203, while in other embodiments, a torus-shaped pocket surrounds a center portion of body 210 to provide this functionality. Further descriptions of such structures are provided below in the description of FIG. 4.

In other embodiments (not shown), an aperture that is not part of such bubble features is provided in any of the embodiments described herein, where the aperture surrounds the expected focal point of the image light, to serve as a spatial filter, blocking light that is not part of the focussed stimulation-light image.

Figure 2D:
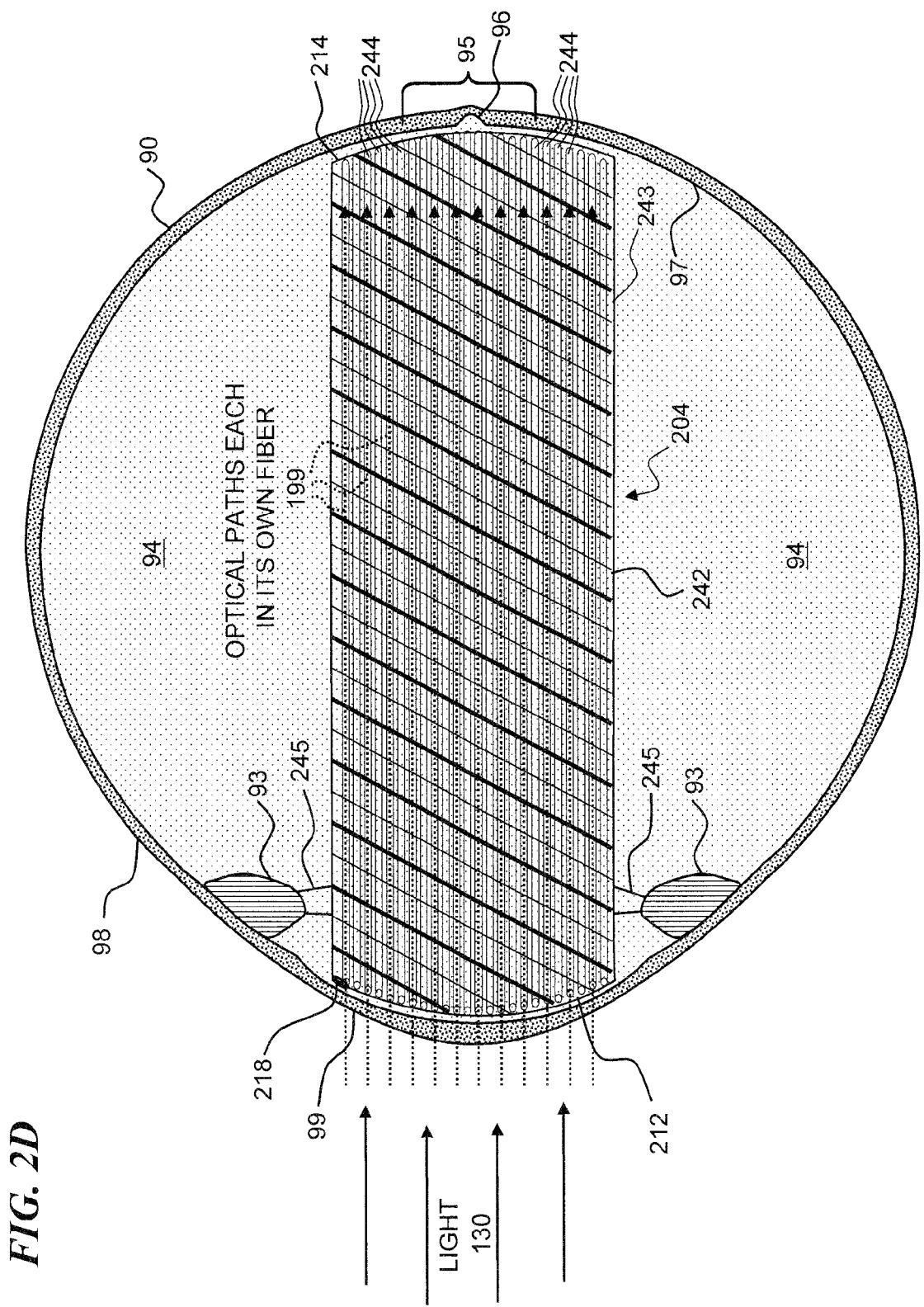
FIG. 2D is a side cross-section view of an eye 90 that illustrates an implanted intra-ocular unit 204 having an embedded optical-fiber bundle, according to some embodiments of the invention.

FIG. 2D is a side cross-section view of an eye 90 that illustrates an implanted intra-ocular unit 204 having an embedded optical-fiber bundle, according to some embodiments of the invention. In some embodiments, the body of the intraocular unit 242 includes a plurality of optical fibers 244 embedded in a carrier 243 of PMMA 243. Each optical fiber 244 provides a separate optical path 199 through the intraocular unit 242. In some embodiments, the plurality of optical fibers 244 are arranged in an array that preserves the image aspect ratio. An image from the light source 130 is formed on the anterior end 212 of the intraocular implant, the image is conducted through the optical fibers 244, and the image is projected from the posterior end 214 of the ocular implant onto the retinal nerves. In some embodiments, the optical fibers 244 are substantially parallel (e.g., the output image exiting the posterior end 214 is the same size and shape as the input image entering at anterior end 212). In other embodiments, the optical fibers 244 have varying non-parallel paths through the carrier 243 (e.g., in some embodiments, the optical fibers 244 themselves remain a constant-diameter size but their spacings increase towards the posterior end such that the fibers diverge (gradually separate from one another towards the posterior end 214) such that the height and/or width of the output image exiting the posterior end 214 is larger than the input image entering at anterior end 212, while in other embodiments, in some embodiments, the optical fibers converge (gradually get closer to one another) such that output image exiting the posterior end 214 is smaller than the input image entering at anterior end 212). In some embodiments, a plurality of optical fibers 244 is gathered in a tight bundle, then one end is heated and stretched away from the opposite end such that the stretched end becomes smaller in diameter while preserving the aspect ratio of the image that is transmitted through the bundle, but the size changes (becoming larger or smaller depending on which end the image enters), since the diameter of each fiber changes, and the diameter of the bundle as a whole changes.

In some embodiments, the body 242 of the intraocular implant is shaped substantially like a cylinder. In other embodiments (not shown, but in a manner similar to FIG. 3), the body 242 of the intraocular implant has a substantially conical shape wherein the posterior end 214 of the body 242 has a larger diameter than the anterior end 212 of the body 242. In further embodiments (not shown), the body 242 of the intraocular implant has a substantially conical shape wherein the anterior end 212 of the body 242 has a larger diameter than the posterior end 214 of the body 242. In some embodiments, the optical fibers 244 are glass and are fabricated from a material that is substantially transparent (transmits at least about 50% of the light energy) to wavelengths of light in the infrared region of about 1000 nm to about 2100 nm (or at least in the portion of that infrared spectrum that is used by the stimulation light signal). In some embodiments, the optical fibers 244 are fabricated from a material that is substantially transparent (transmits at least about 50% of the light energy) to wavelengths of light in the infrared region of about 1600 nm to about 2000 nm. In some embodiments, the optical fibers 244 are fabricated from a material that is substantially transparent to wavelengths of light in the infrared region of about 1700 nm to about 1900 nm. In some embodiments, the optical fibers 244 are fabricated from a material that is substantially transparent to wavelengths of light in the infrared region of about 1800 nm to about 2000 nm. In some embodiments, the optical fibers 244 are fabricated from a material that is substantially transparent to wavelengths of light in the infrared region of about 1800 nm to about 1900 nm.

Figure 3:
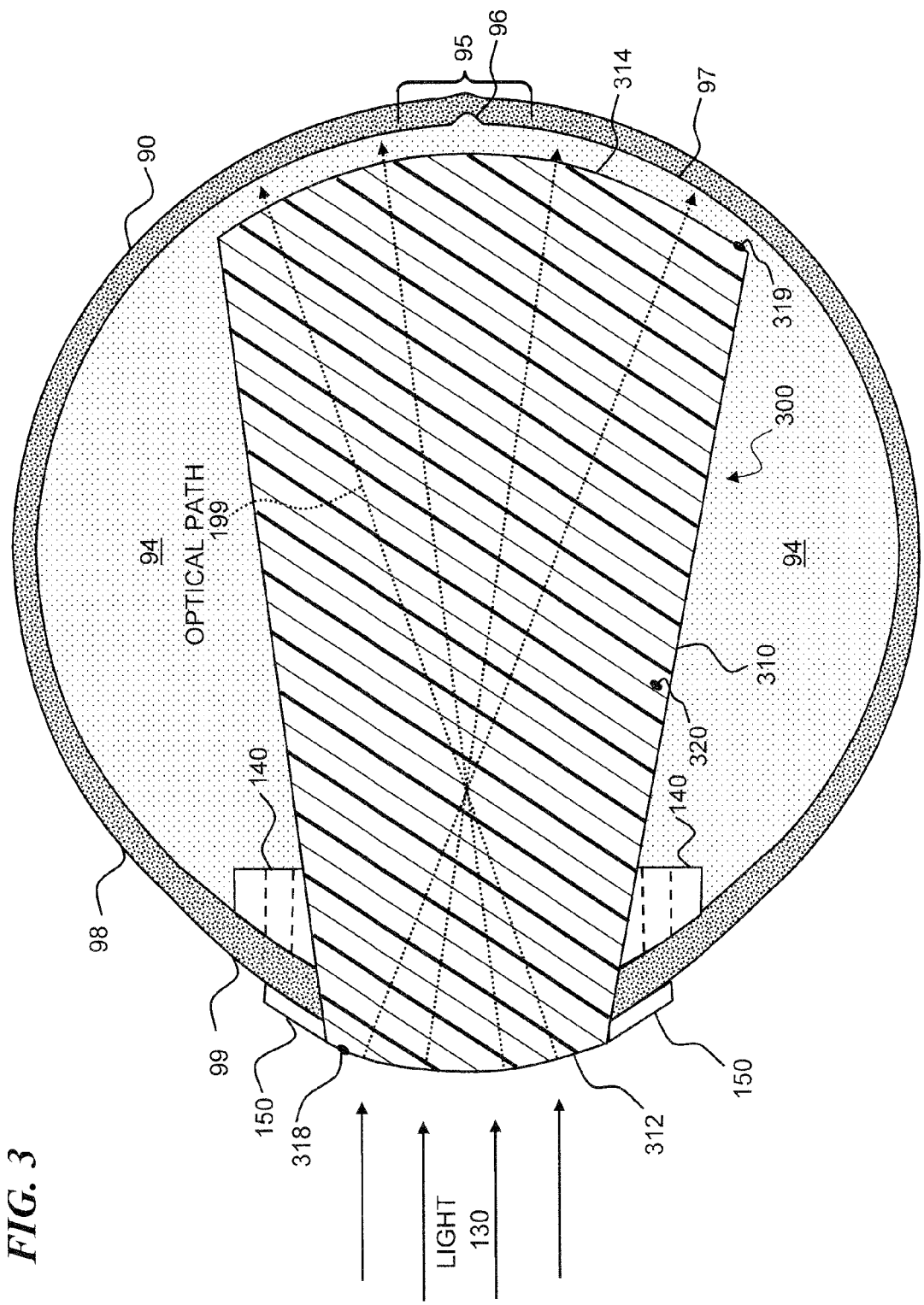
FIG. 3 is a side cross-section view of an eye 90 that illustrates an implanted ocular unit 300 according to some embodiments of the invention.

FIG. 3 is a side cross-section view of an eye 90 that illustrates an implanted ocular unit 300 according to some embodiments of the invention. In some embodiments the ocular unit 300 includes image pipe 310 that has a substantially conical, or tapered, shape rather than the cylindrical shape (e.g., as shown in ocular unit 100 in FIGS. 1A and 1B and ocular unit 201 in FIG. 2A and ocular unit 202 of FIG. 2B) in order to provide stimulating light over a larger area of the retina for a wider field of view. In some such embodiments, the posterior end 314 of the transparent material of image pipe 310 has a diameter that is larger than a diameter of the anterior end 312 of the transparent material. In some embodiments, the ocular unit 300 includes a light-transparent pathway or "image pipe" 310 for transmitting a stimulation pattern of infrared light 130 from an external stimulator array through the eye, the ocular unit 300 having a light-receiving anterior end 312 closest to the eye's anterior surface and extending to a posterior end 314 of image pipe 310 closer to the fovea 96 than to the eye's anterior surface, projecting an image on the retina 97, including on the macula 95 and fovea 96.

In some embodiments, one or both ends of the image pipe 310 are shaped to focus the externally generated stimulator-array signals on the retina and fovea. In some embodiments, there is an external two-dimensional array VCSEL-array IR stimulator providing IR light 130 into the anterior end of the ocular implant 300. In some embodiments, there is an external two-dimensional array IR stimulator for each eye to help provide three-dimensional images to the user with an ocular unit 300 implanted in each eye. In some embodiments, image pipe 310 includes a lens (see, for example, lens 216 of FIG. 2A) with a different index of refraction than the rest of image pipe 310, to focus the image on the retina 97. In some embodiments, the lens inverts the incoming image and focuses the image on the retina. In some other embodiments, on the lens is noninverting and directs collimated light on the retina. In some embodiments, the image pipe 310, lens, in combination with an external laser-signal generation device produce an inverted nerve-stimulation pattern on the retina, similar to the inverted image a normal human eye.

In some embodiments, ocular unit 300 has the optional features of ocular unit 100 and intra-ocular unit 201, with the difference being the conical-shaped image pipe 310. In some embodiments, ocular unit 201 includes a conical-shaped image pipe instead of the cylindrically shaped image pipe 210 shown in FIG. 2A and FIG. 2B.

Figure 4:
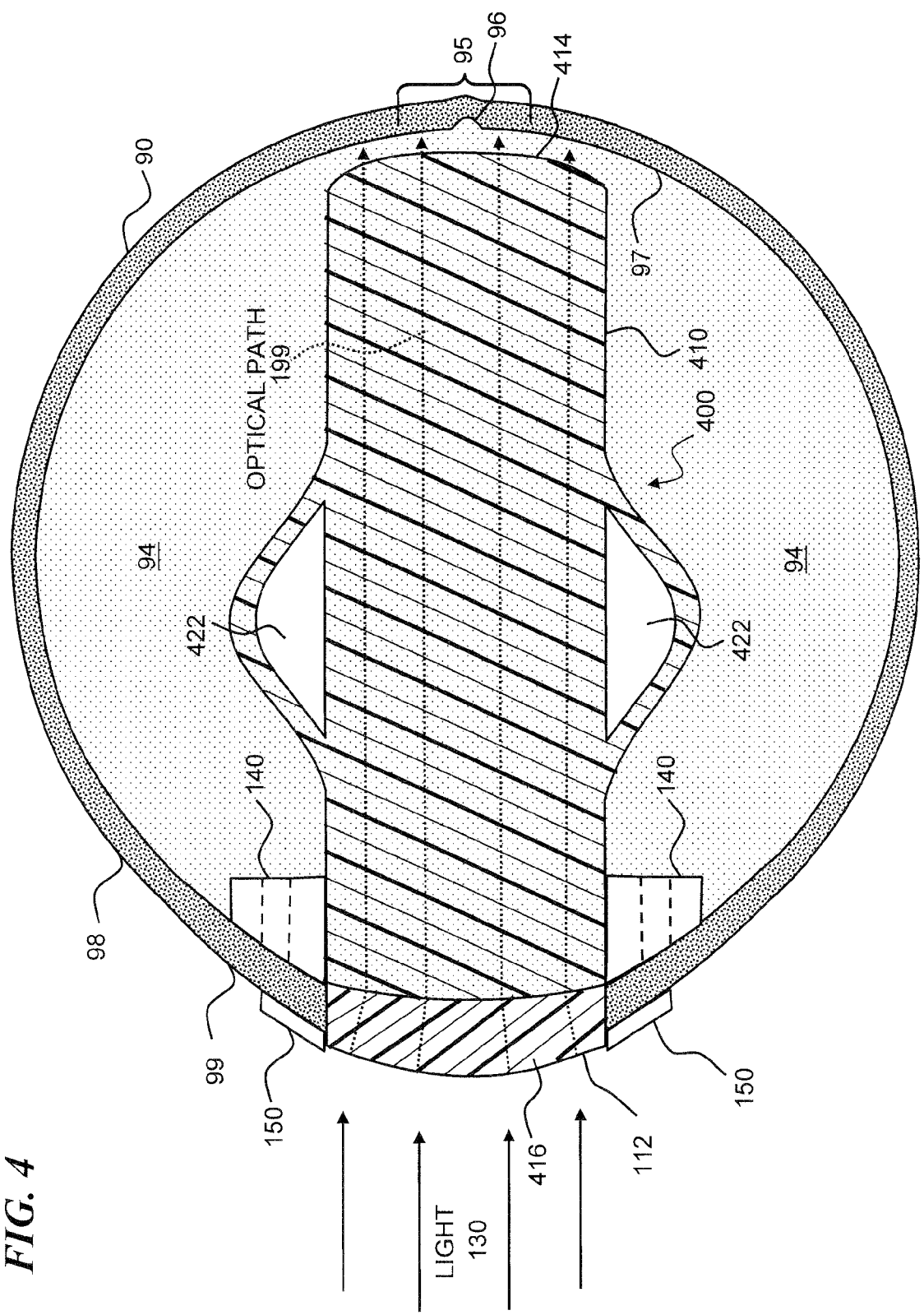
FIG. 4 is a side cross-section view of an eye 90 that illustrates an implanted ocular unit 400 according to some embodiments of the invention.

FIG. 4 is a side cross-section view of an eye 90 that illustrates an implanted ocular unit 400 according to some embodiments of the invention. In some embodiments the ocular unit 400 includes image pipe 410 that has a substantially cylindrical shape with an additional widened section including a doughnut-shaped (i.e., torus-shaped) hollow portion 422 that surrounds the longitudinal axis of the optical path 199. In some such embodiments, the posterior end 414 of the transparent material of image pipe 410 has a diameter about the same diameter as the anterior end 412 of the transparent material. In some embodiments, the ocular unit 400 includes a light-transparent pathway or "image pipe" 410 for transmitting a stimulation pattern of infrared light 130 from an external stimulator array through the eye, the ocular unit 400 having a light-receiving anterior end 412 closest to the eye's anterior surface and extending to a posterior end 414 of image pipe 410 closer to the fovea 96 than to the eye's anterior surface, projecting an image on the retina 97, including on the macula 95 and fovea 96.

To more closely match the density of the vitreous humor, some embodiments of image pipe 410 include at least one hollow portion 422 such that the overall density of the image pipe 410 is the same as the density of the surrounding vitreous humor and the center of mass of the image pipe 410 coincides with the center of rotation of the eye, in order that the image pipe 410 does not tend to move relative to the eye with movement. In some embodiments, the hollow portion 422 is filled with an inert gas. In some embodiments, the hollow portion is filled with a low-pressure gas having a pressure of no more than about 1000 Torr.

The placement, size, and shape of the hollow portion in the image pipe 410 is used in some embodiments to not only match the density of the vitreous humor but to also control the center of gravity to help provide a more stable implant the is resistant to movement of the head or eyeball. In some embodiments, the light-transmitting portion of image pipe 410 is solid material and the hollow portion is formed in a peripheral portion outside and surrounding the light-transmitting path. This configuration reduces the number of optical interfaces in the light path. In some embodiments, the light-transmitting portion of image pipe 410 is solid material and the hollow portion 422 is formed symmetrically around a peripheral portion outside and surrounding the light-transmitting path, such that regardless of whether the person's head is upright or is lying on one side, there is no rotational or other force acting to move the implant (i.e., image pipe 410) relative to the eye. In other embodiments, the hollow portion is formed in (or is very slightly larger in) a top portion of image pipe 410, in order to help keep the image pipe 410 upright and in the desired position when the patient's head is upright.

In some embodiments, image pipe 410 includes a lens 416, with a different index of refraction than the rest of image pipe 410, to focus the image on the retina 97. In some embodiments (as shown by lens 216 in FIG. 2C), the lens inverts the incoming image and focuses the image through a focal point and onto the retina. In some other embodiments (as shown in FIG. 4), the lens 416 is noninverting and directs collimated light on the retina. In still other embodiments, the lens is noninverting and directs diverging light (such as the lens 217 shown in FIG. 2B), or converging light (embodiments not shown herein) on the retina. In some embodiments, the image pipe 410, lens 416, in combination with an external laser-signal generation device produce an inverted nerve-stimulation pattern on the retina, similar to the inverted image a normal human eye.

In some embodiments, ocular unit 400 is fully contained intraocularly (i.e., completely inside the eye similar to ocular unit 201 of FIG. 2A) after being surgically implanted. In some such embodiments, the image pipe 410 is surgically secured in place in the eye with the implant sewn, stapled, or otherwise secured to the ciliary muscle or secured to other internal parts of the eye to hold it securely in place. In some such embodiments, the ocular unit 400 is completely contained within the eye and the user's cornea 99 is maintained intact.

FIG. 5A is a side cross-section view of an eye 90 that illustrates an implanted ocular unit 501 according to some embodiments of the invention. In some embodiments the ocular unit 501 includes image pipe 510 that has a substantially cylindrical shape with a short hollow center portion 522A. In some such embodiments, the posterior end 514 of the transparent material of image pipe 510 has a diameter about the same diameter as the anterior end 512 of the transparent material. In some embodiments, the ocular unit 501 includes a light-transparent pathway or "image pipe" 510 for transmitting a stimulation pattern of infrared light 130 from an external stimulator array through the eye, the ocular unit 501 having a light-receiving anterior end 512 closest to the eye's anterior surface and extending to a posterior end 514 of image pipe 510 closer to the fovea 96 than to the eye's anterior surface, projecting an image on the retina 97, including on the macula 95 and fovea 96.

To more closely match the density of the vitreous humor, some embodiments of image pipe 510 include at least one hollow portion 522A such that the overall density of the image pipe 510 is the same as the density of the surrounding vitreous humor and the center of mass of the image pipe 510 coincides with the center of rotation of the eye, in order that the image pipe 510 does not tend to move relative to the eye with movement. In some embodiments, the hollow portion 522A is filled with an inert gas. In some embodiments, the hollow portion 522A is filled with a low-pressure gas having a pressure of no more than about 1000 Torr.

The placement, size, and shape of the hollow portion 522A in the image pipe 510 is used in some embodiments to not only match the density of the vitreous humor but to also control the center of gravity (e.g., to balance relative to the mass of lens 516) to help provide a more stable implant the is resistant to movement of the head or eyeball. In some embodiments, the light-transmitting portion of image pipe 510 is solid material and the hollow portion is formed in a central portion of the light-transmitting path. In other embodiments, the hollow portion is formed in (or is very slightly larger in) a top portion of image pipe 110, in order to help keep the image pipe 510 upright and in the desired position when the patient's head is upright.

In some embodiments, image pipe 510 includes a lens 516, with a different index of refraction than the rest of image pipe 510, to focus the image on the retina 97. In some embodiments, the lens inverts the incoming image and focuses the image on the retina. In some other embodiments, on the lens is noninverting and directs collimated light on the retina. In some embodiments, the image pipe 510, lens 516, in combination with an external laser-signal generation device 180 produce an inverted nerve-stimulation pattern on the retina, similar to the inverted image a normal human eye.

In some embodiments, ocular unit 501 is fully contained intraocularly (i.e., completely inside the eye similar to ocular unit 201) after being surgically implanted. In some such embodiments, the image pipe 510 is surgically secured in place in the eye with the implant sewn, stapled, or otherwise secured to the ciliary muscle or secured to other internal parts of the eye to hold it securely in place. In some such embodiments, the ocular unit 501 is completely contained within the eye and the user's cornea 99 is maintained intact.

Figure 5B:
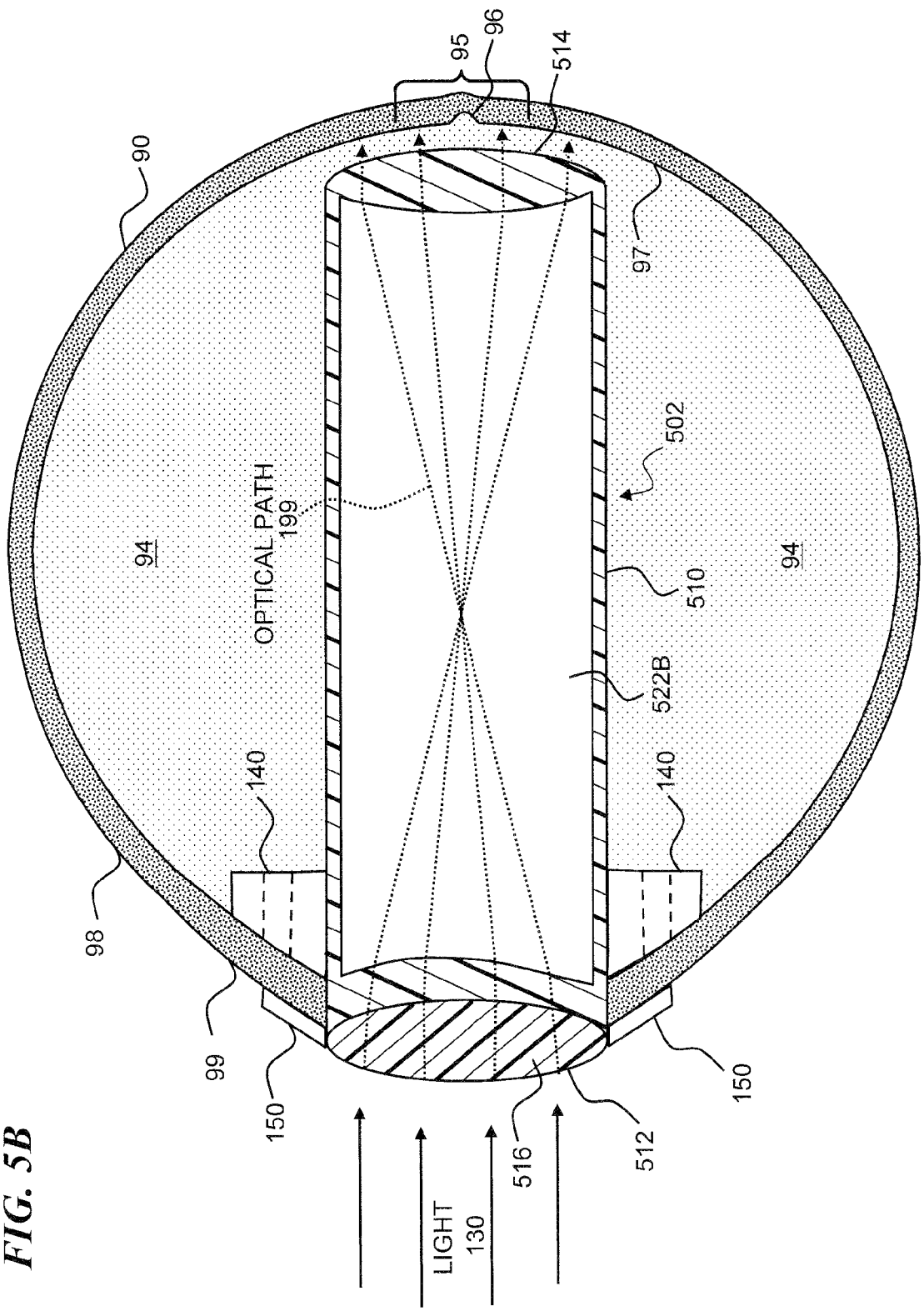
FIG. 5B is a side cross-section view of an eye 90 that illustrates an implanted ocular unit 502 according to some embodiments of the invention.

FIG. 5B is a side cross-section view of an eye 90 that illustrates an implanted ocular unit 502 according to some embodiments of the invention. In some embodiments the ocular unit 502 includes image pipe 510 that has a substantially cylindrical shape with a long hollow center portion 522B. In some embodiments, implanted ocular unit 502 is substantially similar to ocular unit 501 of FIG. 5A described above, except that ocular unit 502 has a longer hollow center portion 522B.

Figure 5C:
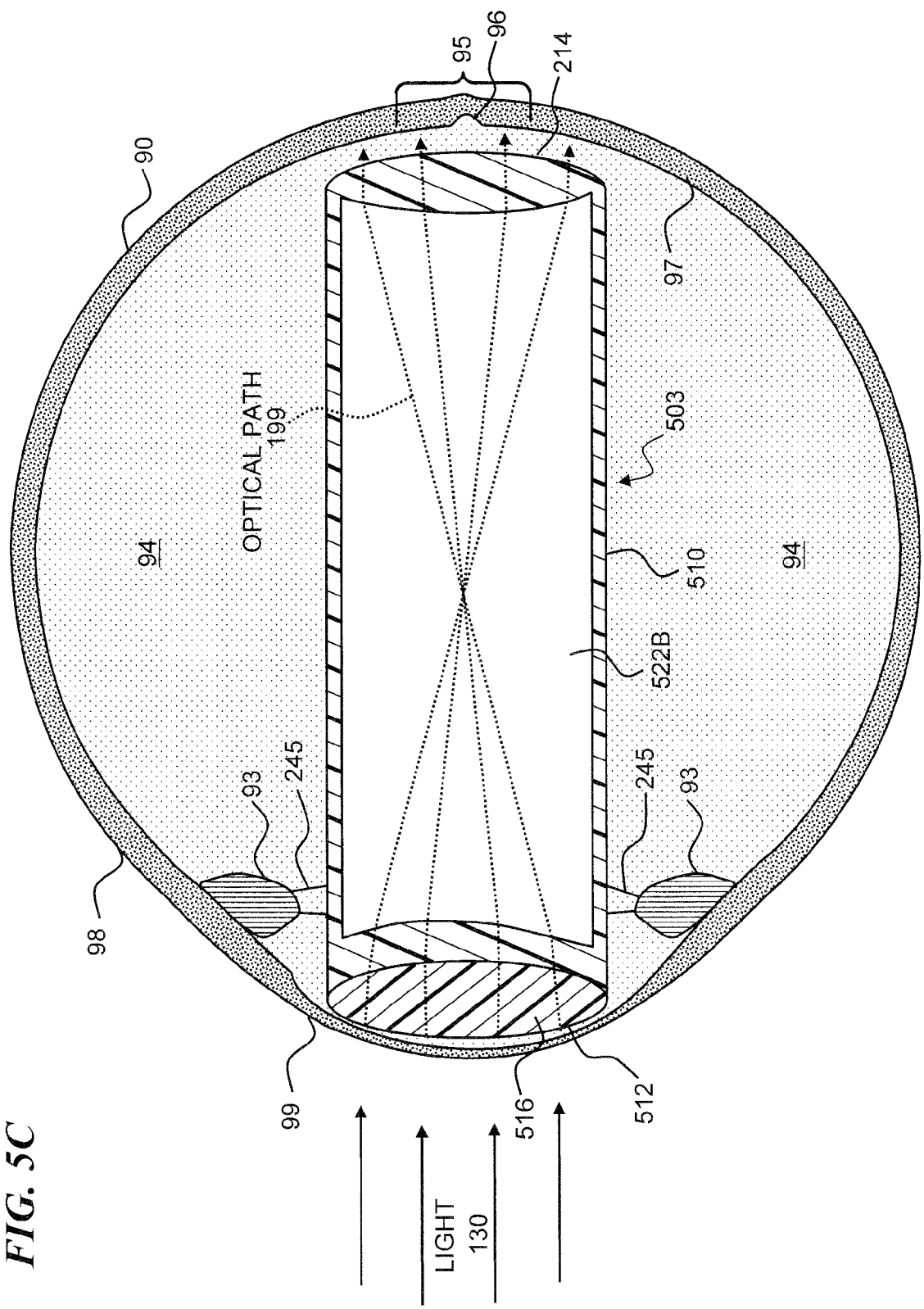
FIG. 5C is a side cross-section view of an eye 90 that illustrates an implanted ocular unit 503 according to some embodiments of the invention.

FIG. 5C is a side cross-section view of an eye 90 that illustrates an implanted ocular unit 503 according to some embodiments of the invention. In some embodiments the ocular unit 503 includes image pipe 510 that has a substantially cylindrical shape with a long hollow center portion 522B. In some embodiments, implanted ocular unit 503 is substantially similar to ocular unit 502 of FIG. 5B, except that ocular unit 503 is implanted entirely within the eye 90 as was the case with ocular unit 203 of FIG. 2C described above.

Figure 6:
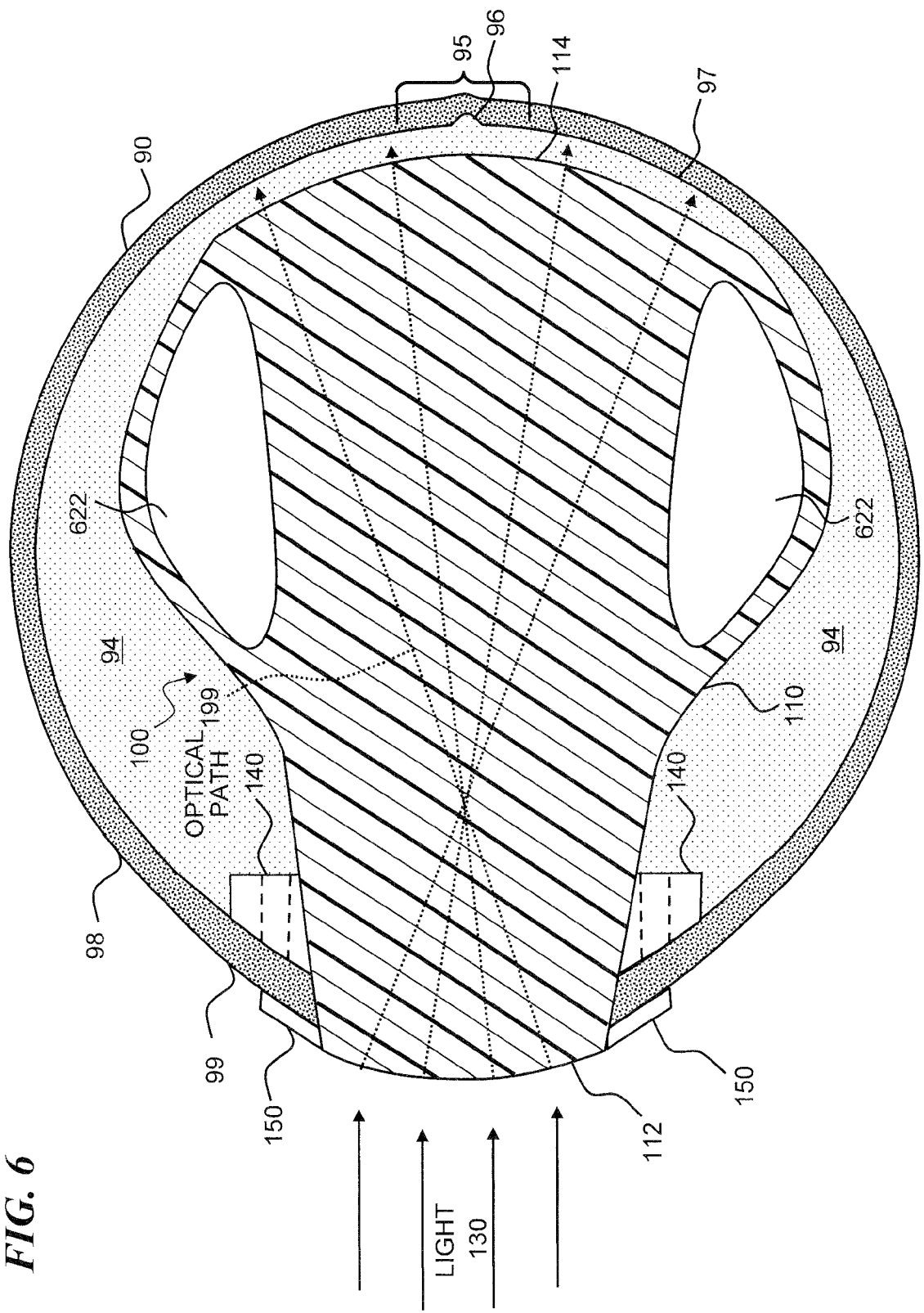
FIG. 6 is a side cross-section view of an eye 90 that illustrates an implanted ocular unit 600 according to some embodiments of the invention.

FIG. 6 is a side cross-section view of an eye 90 that illustrates an implanted ocular unit 600 according to some embodiments of the invention. In some embodiments the ocular unit 600 includes image pipe 610 that has a substantially conical shape with an additional widened section including a doughnut-shaped hollow portion 622. In some such embodiments, the posterior end 614 of the transparent material of image pipe 610 has a diameter substantially larger than the diameter as the anterior end 612 of the transparent material. In some embodiments, the ocular unit 600 includes a light-transparent pathway or "image pipe" 610 for transmitting a stimulation pattern of infrared light 130 from an external stimulator array through the eye, the ocular unit 600 having a light-receiving anterior end 612 closest to the eye's anterior surface and extending to a posterior end 614 of image pipe 610 closer to the fovea 96 than to the eye's anterior surface, projecting an image on the retina 97, including on the macula 95 and fovea 96.

To more closely match the density of the vitreous humor, some embodiments of image pipe 610 include at least one hollow portion 622 such that the overall density of the image pipe 610 is the same as the density of the surrounding vitreous humor and the center of mass of the image pipe 610 coincides with the center of rotation of the eye, in order that the image pipe 610 does not tend to move relative to the eye with movement. In some embodiments, the hollow portion 622 is filled with an inert gas. In some embodiments, the hollow portion is filled with a low-pressure gas having a pressure of no more than about 1000 Torr.

The placement, size, and shape of the hollow portion in the image pipe 610 is used in some embodiments to not only match the density of the vitreous humor but to also control the center of gravity to help provide a more stable implant the is resistant to movement of the head or eyeball. In some embodiments, the light-transmitting portion of image pipe 610 is solid material and the hollow portion is formed in a peripheral portion outside and surrounding the light-transmitting path. This configuration reduces the number of optical interfaces in the light path. In some embodiments, the light-transmitting portion of image pipe 610 is solid material and the hollow portion 422 is formed symmetrically around a peripheral portion outside and surrounding the light-transmitting path, such that regardless of whether the person's head is upright or is lying on one side, there is no rotational or other force acting to move the implant (i.e., image pipe 610) relative to the eye. In other embodiments, the hollow portion is formed in (or is very slightly larger in) a top portion of image pipe 610, in order to help keep the image pipe 610 upright and in the desired position when the patient's head is upright.

In some embodiments, image pipe 610 includes a lens (see, for example, lens 216 of FIG. 2A) with a different index of refraction than the rest of image pipe 610, to focus the image on the retina 97. In some embodiments, the lens inverts the incoming image and focuses the image on the retina. In some other embodiments, on the lens is noninverting and directs collimated light on the retina. In some embodiments, the image pipe 610, lens, in combination with an external laser-signal generation device produce an inverted nerve-stimulation pattern on the retina, similar to the inverted image a normal human eye.

In some embodiments, ocular unit 600 is fully contained intraocularly (i.e., completely inside the eye similar to ocular unit 600) after being surgically implanted. In some such embodiments, the image pipe 610 is surgically secured in place in the eye with the implant sewn, stapled, or otherwise secured to the ciliary muscle or secured to other internal parts of the eye to hold it securely in place. In some such embodiments, the ocular unit 600 is completely contained within the eye and the user's cornea 99 is maintained intact.

Figure 7:
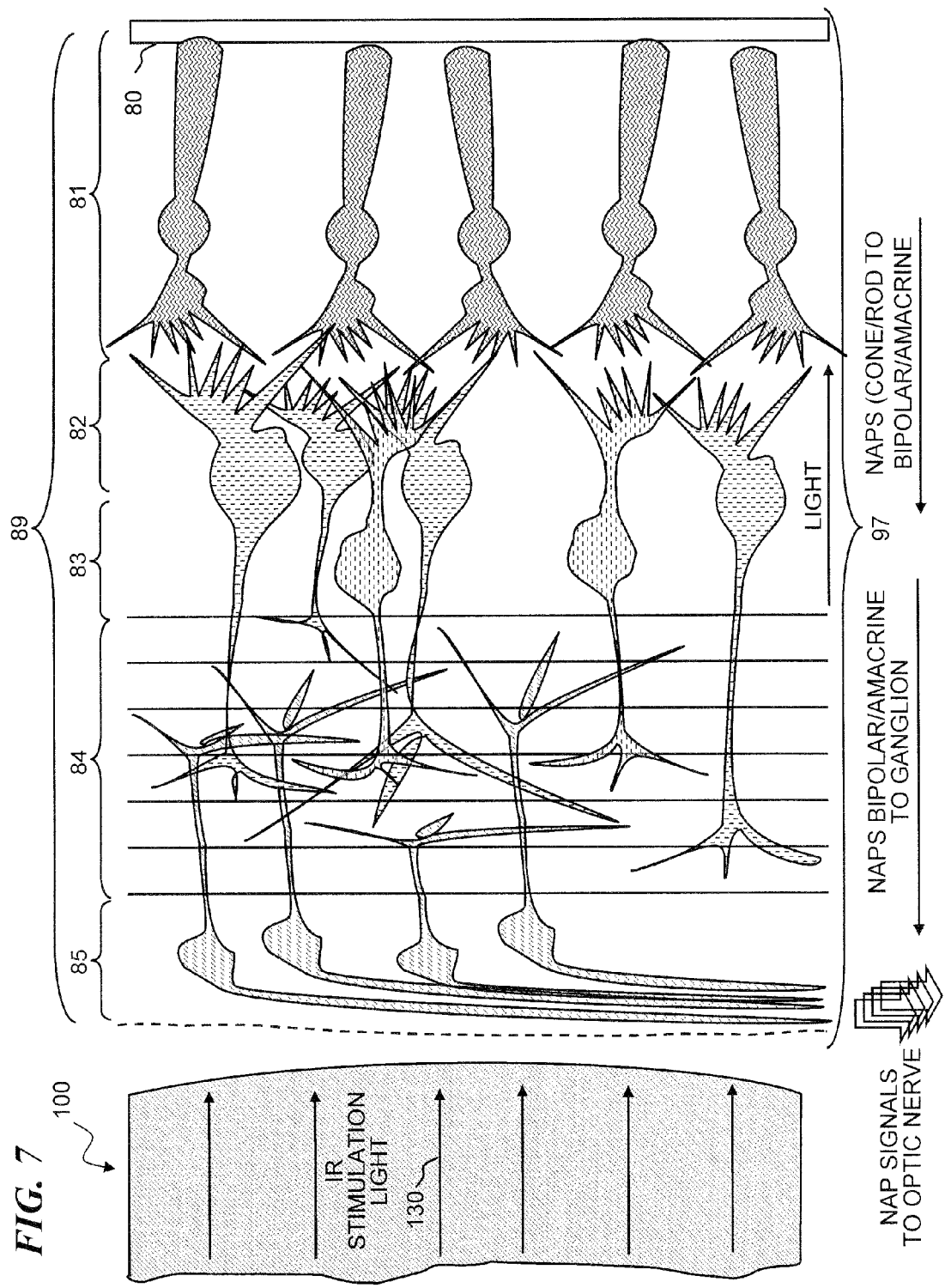
FIG. 7 is a side cross-section view of a retina 97.

FIG. 7 is a side cross-section view of a retina 97. In some embodiments, the present invention is used to stimulate nerve action potentials directly in the ganglion nerves 85, the amacrine nerve cells 83, and/or the bipolar nerve cells 82 of the retina 97. According to Frank Werblin and Botond Roska, in an article titled "The Movies in Our Eyes" (Scientific American, April 2007, pages 72-79), it appears that normally the rod cells and cone cells 81 at the posterior wall 80 of the retina 97 receive visible light (having wavelengths in the range of 400 to 700 nm), and generate nerve signals to a plurality of synapses at the tips of its axons. These signals from one rod or cone cell are received by the bipolar cells 82 and amacrine cells 83 that are in direct contact with the synapses of that rod or cone cell 81. They note that researchers have identified numerous types of bipolar cells 82, numerous types of amacrine cells 83, and numerous types of ganglion cells 85. The bipolar cells generate excitory signals based on inputs from the rods and cones to which each bipolar cell is connected, while the amacrine cells generate inhibitory signals based on inputs from the rods and cones to which each amacrine cell is connected. There are a plurality of connection layers in the inner plexiform layer 84, wherein at each connection layer has transmit ends of axons from various excitory bipolar cells and inhibitory amacrine cells, to which are connected the receive ends of the ganglion cells. In some embodiments, different signals from the IR stimulation light are focussed on different ones of either ganglion, amacrine, or bipolar cells.

When focussed on the ganglion layer of cells 85, the IR stimulation light signals generate nerve action potentials (NAPs) directly in ones of those ganglion cells, which NAPs are then transmitted toward the optic nerve output of the eye. When focussed on the bipolar layer of cells 82, the IR stimulation light signals generate excitory nerve action potentials (NAPs) directly in ones of those bipolar cells, which excitory NAPs are then transmitted toward one of the layers of interconnects in the inner plexiform layer 84, where once they combine and reach a certain threshold they then trigger a NAP in the respective ganglion cell(s). In contrast, when focussed on the amacrine layer of cells 83, the IR stimulation light signals generate inhibitory nerve action potentials (NAPs) directly in ones of those amacrine cells, which inhibitory NAPs are then transmitted toward one of the layers of interconnects in the inner plexiform layer 84, where once they act to inhibit NAP in the respective ganglion cell(s). In some embodiments, the stimulation light signals are transmitted from differing distances from the anterior (light-entry) end of the ocular implant, and thus they focus at differing distances from the posterior end of the ocular implant, and thus can be controlled as to which layer of nerve cells they will stimulate. Accordingly, NAPs can be controllably and selectively triggered in different layers of nerve cells in the retina, to thus generate NAPs that are either excitory (from the bipolar cell layer 82) or inhibitory (from the amacrine layer of cells 83) and those NAPS are then additively and/or subtractively combined in the inner plexiform layer to trigger output signals in the ganglion cells connected to those inner plexiform layer connections, or directly output (from the ganglion layer of cells 85) when the stimulation light is focussed there.

In some embodiments, the external stimulation IR source outputs IR light signals that represent a pre-processed version of an image scene, wherein the preprocessing mimics or replicates the internal optical processing of images normally performed by the millions of interconnections between the various cell layers of the retina. In some embodiments, the preprocessing needed is empirically determined by focussing various patterns on different ones of the cells in the various bipolar, amacrine and/or ganglion layers and having the subjects report the sensation perceived, and/or by actually measuring NAPs in the tissue of eyes of lab subjects. By triggering NAPs in the various nerve-cell layers 82, 83, and/or 85, certain degeneration effects, defects or diseases that cause loss of vision can be bypassed by triggering NAPs in the anterior layers of cells of the retina.

In other embodiments, the IR stimulation light is used to trigger NAPs in the rods or cones, and those NAPs are then combined in the normal way of processing by the various bipolar, amacrine and/or ganglion layers.

FIG. 8A is a side cross-section view of a stimulation system 801 that uses a single-depth VCSEL array 887 and a holographic imager 811. In some embodiments, the stimulation light 130 emitted by the stimulation light sources (e.g., in some embodiments, an array of independently addressable and separately activatable vertical-cavity surface-emitting lasers (VCSELs) 885 (optionally each including a focussing element 886 such as a lens or holograph) implemented on one or more semiconductor chips 887 is of a narrow-linewidth single wavelength laser light. This single wavelength light facilitates focussing using holographs. In some embodiments, a holograph 811 is implemented on the anterior surface 112 of ocular unit 801. In some embodiments, holograph 811 facilitates focussing the stimulation light at different layers (e.g., various nerve-cell layers 82, 83, and/or 85 and/or the cone/rod cells of optical-cell layer 81) of the retina 97. In some embodiments, all of the VCSELs 85 are implemented at a single depth (as a single plane of emission at the surface of chip 887). In some embodiments, holograph 811 is created by doing a numerical simulation of the light sources at the surface plane of the VCSEL array chip 887 and a plurality of layers at different depths in the retina, in order that various light source points can be activated to trigger NAPs at selected layers (e.g., cell layers 81, 82, 83, and/or 85) and selected Cartesian coordinates on the retina 97 (i.e., at the three-dimensional coordinate of the desired cells to be stimulated).

FIG. 8B is a side cross-section view of a stimulation system 802 that uses a VCSEL array 888 having a plurality of depths and a holographic imager 812. In some embodiments, the VCSELs 85 are implemented at a plurality of depths (as a plurality of planes of emission at the surface of chip 887). In some such embodiments, by having different planes of emission (by having the emission face of the VCSELs 885 at different levels, and/or by having the focussing lenses 886 have different heights from the chip or different focal lengths, or other suitable configuration), the ocular unit's focussing element (e.g., lens 116 of FIG. 1A or holograph 812 of FIG. 8B) can focus the light from the different emission planes onto different layers of cells (e.g., the ganglion nerve cells 85, the amacrine nerve cells 83, and/or the bipolar nerve cells 82, and/or the cone/rod cells of optical-wavelength-detecting cell layer 81) in the retina 97. In some embodiments, holograph 812 is created by doing a numerical simulation of the light sources at the plurality of emission planes of the VCSEL array chip 887 and a plurality of layers at different depths in the retina, in order that various light source points can be activated to trigger NAPs at selected layers (e.g., cell layers 81, 82, 83, and/or 85) and selected Cartesian coordinates on the retina 97 (i.e., at the three-dimensional coordinate of the desired cells to be stimulated).

Figure 9:
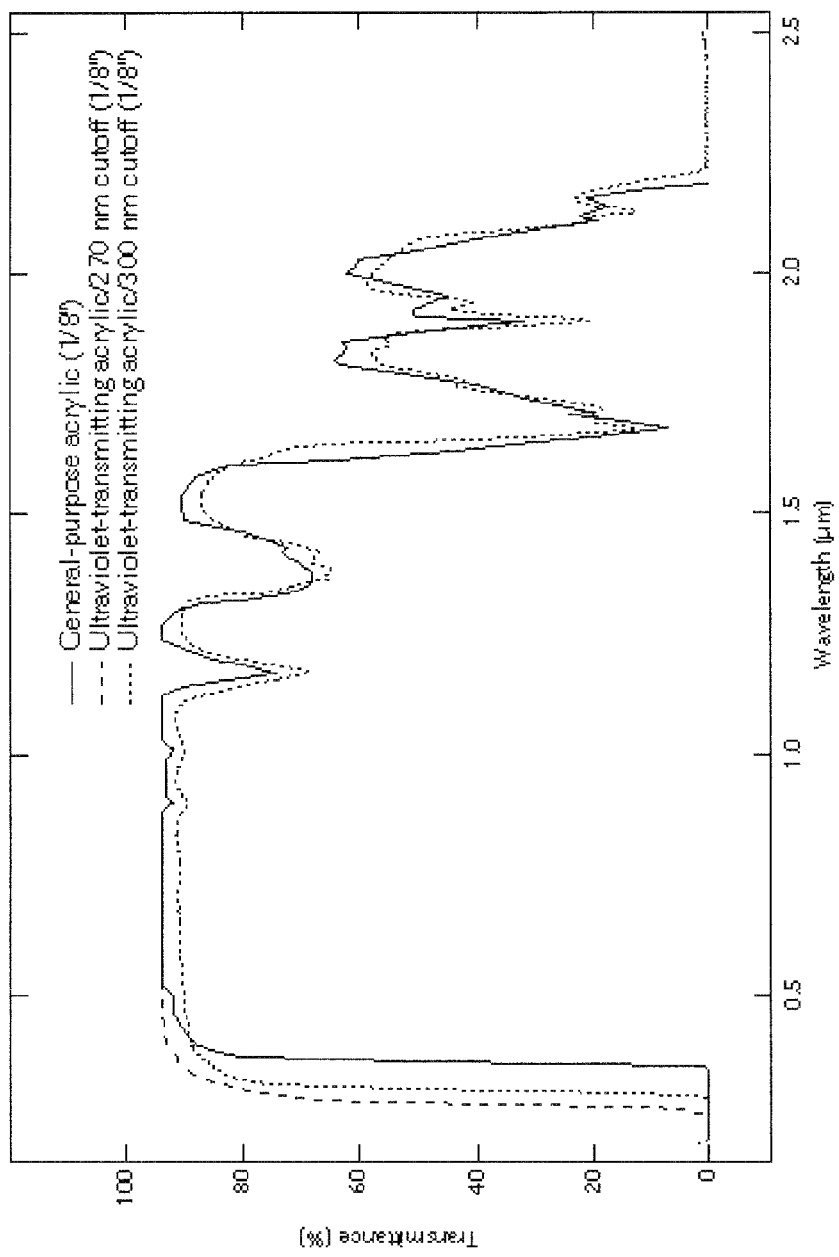
FIG. 9 is a graph showing the absorption of light by PMMA at various wavelengths.

FIG. 9 is a graph that shows the transmittance of light with wavelengths of 0.5 microns to 2.5 microns through a typical commercially available acrylic (PMMA) material. This specific data is from a one-eighth-inch (3.17 mm)-thick piece of an acrylic (PMMA) product available from Fresnel Technologies, Inc. in Fort Worth, Tex. It can be seen that the amount of light transmitted through the PMMA material varies considerably with the wavelength of light, from 90 percent or more transmitted at shorter wavelengths (e.g., less than 1.2-micron wavelengths) to almost none at some longer wavelengths (e.g., greater than 2.2-micron wavelengths). Throughout the infrared region of about 1000 nm (shown as 1.0 μm on the graph) to 2000 nm (2.0 μm), there are sharp peaks and valleys of transmittance. In some embodiments, a polymer material is used that has a relatively high transmittance at the wavelengths used by the present invention (greater than 50% of the incident light is transmitted out the posterior end). In some embodiments, a polymer material (such as PMMA) having a high biocompatibility is used as an outer layer or coating on the ocular implant, and a different material (such as glass or another polymer) is used for most of the light-transmission path in the case where the coating material is not transparent enough at the wavelengths used, or where the coating material has a density (mass-per-volume) that is different than what is wanted (e.g., a density that matches the density of the fluids in the eye).

Figure 10:
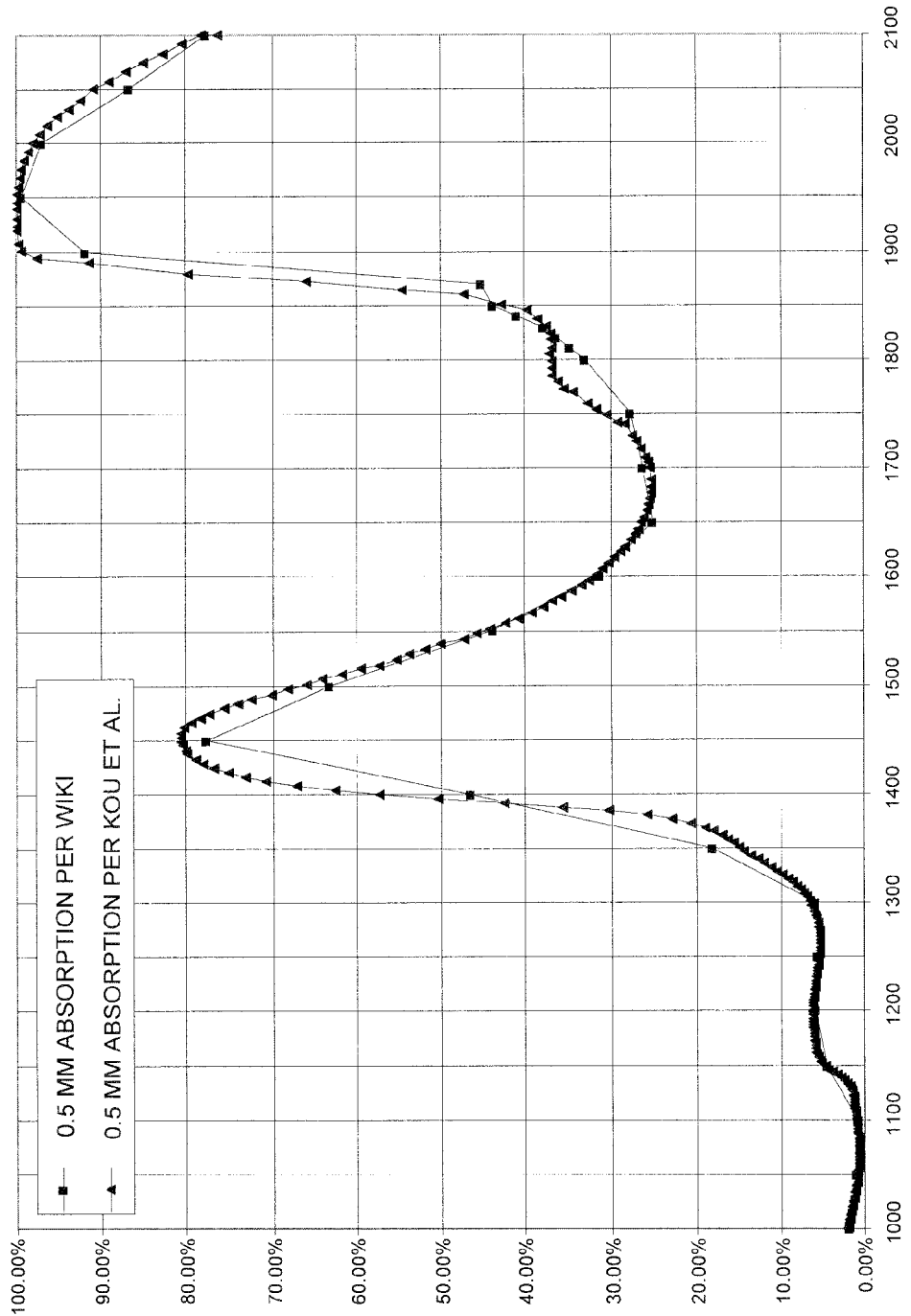
FIG. 10 is a graph showing two sets of measurements of the absorption of light by 0.5 mm of water at wavelengths of light between 1000 and 2100 nm (infrared).

FIG. 10 is a graph showing the absorption of light with various wavelengths in a range of 1000 nm to 2100 nm (output intensity as a percent of the input intensity) for a 0.5-mm-thick layer of water. As with PMMA, the amount of light transmitted though water varies considerably over this range of light wavelengths, with multiple peaks of absorption. The vitreous humor of an eye is 98-99% water, so this graph, showing the absorption by water, approximates the absorption of various wavelengths of infrared light in vitreous humor.

Neurons that make up the retina of an eye can be directly stimulated by light such that NAPs or CNAPs are triggered. The NAP or CNAP response of the neurons depends on the energy (power times pulse duration) absorbed per unit area and wavelength (absorption by various tissues varies as a function of wavelength) of the light pulses impinging on and thereby directly stimulating the neurons. Neurons are sensitive to wavelengths of light in the range of about 1800 nm to about 1900 nm. FIG. 9 illustrates that PMMA has a relatively high transmittance in most of this wavelength range so it is a good choice of material for transmitting infrared light from an external light source to the retinal nerves of an eye, in some embodiments. However, FIG. 10 shows that water (and thus vitreous humor) has very high light absorption for wavelengths longer than 1900 nm, and relatively high absorption in much of the wavelength range of between about 1800 nm to about 1900 nm. Thus, some embodiments of the present invention use wavelengths that represent a compromise between wavelengths that are readily absorbed by the nerves to trigger a NAP response, and those that readily pass through the thin layer of vitreous humor at the posterior end of the ocular implant and/or the thin layer of aqueous humor at the anterior end. Locating the respective ends of the intraocular implant close to the front and rear surfaces of an eye results in greater light signal transmission from the external light to the retinal nerves, but benefits from more precisely manufactured components and a more complex surgical implant procedure needed to get a close fit. Conversely, locating the ends of the intraocular implant further from the front and rear surfaces of the eye results in the need for less precisely manufactured components and requires a less complex surgical implant process, and it may be biologically beneficial to increase the fluid adjacent the tissue, but results in a decreased amount of signal light transmitted from the external light source to the retinal nerves of the eye.

In some embodiments, the light-receiving surface portion of the anterior end 212 of the ocular unit (according to any of the above-described embodiments of the present invention) is shaped so as to have a substantially constant spacing from (i.e., to substantially conform to) the inner surface of the cornea of the eye.

In some embodiments, this light-receiving surface portion of the anterior end of the ocular unit is located at a substantially constant spacing of no more than 2.5 mm from the inner surface of the cornea of the eye. In some embodiments, this light-receiving anterior surface portion is located at a substantially constant spacing of no more than 2.0 mm from the inner surface of the cornea of the eye. In some embodiments, this light-receiving anterior surface portion is located at a substantially constant spacing of no more than 1.5 mm from the inner surface of the cornea of the eye. In some embodiments, this light-receiving anterior surface portion is located at a substantially constant spacing of no more than 1.0 mm from the inner surface of the cornea of the eye. In some embodiments, this light-receiving anterior surface portion is located at a substantially constant spacing of no more than 0.5 mm from the inner surface of the cornea of the eye. In some embodiments, this light-receiving anterior surface portion is located no more than 0.2 mm from the inner surface of the cornea of the eye. In some embodiments, this light-receiving anterior surface portion is located at a substantially constant spacing of about 0.5 mm from the inner surface of the cornea of the eye. In some embodiments, this light-receiving anterior surface portion is located at a substantially constant spacing of about 0.2 mm from the inner surface of the cornea of the eye.

In some embodiments, the light-output surface portion of posterior end 214 of the ocular unit (according to any of the above-described embodiments of the present invention) is shaped so as to have a substantially constant spacing from (i.e., to substantially conform to) the ganglion layer of the retina of the eye.

In some embodiments, the light-output surface portion of posterior end of the ocular unit is located at a substantially constant spacing of no more than 2.5 mm from the ganglion layer of the retina of the eye. In some embodiments, this light-output surface portion is located at a substantially constant spacing of no more than 2.0 mm from the ganglion layer of the retina of the eye. In some embodiments, this light-output surface portion is located at a substantially constant spacing of no more than 1.5 mm from the ganglion layer of the retina of the eye. In some embodiments, this light-output surface portion is located at a substantially constant spacing of no more than 1.0 mm from the ganglion layer of the retina of the eye. In some embodiments, this light-output surface portion is located at a substantially constant spacing of no more than 0.5 mm from the ganglion layer of the retina of the eye. In some embodiments, this light-output surface portion is located at a substantially constant spacing of no more than 0.2 mm from the ganglion layer of the retina of the eye. In some embodiments, this light-output surface portion is located at a substantially constant spacing of about 0.5 mm from the ganglion layer of the retina of the eye. In some embodiments, this light-output surface portion is located at a substantially constant spacing of about 0.2 mm from the ganglion layer of the retina of the eye.

Figure 11:
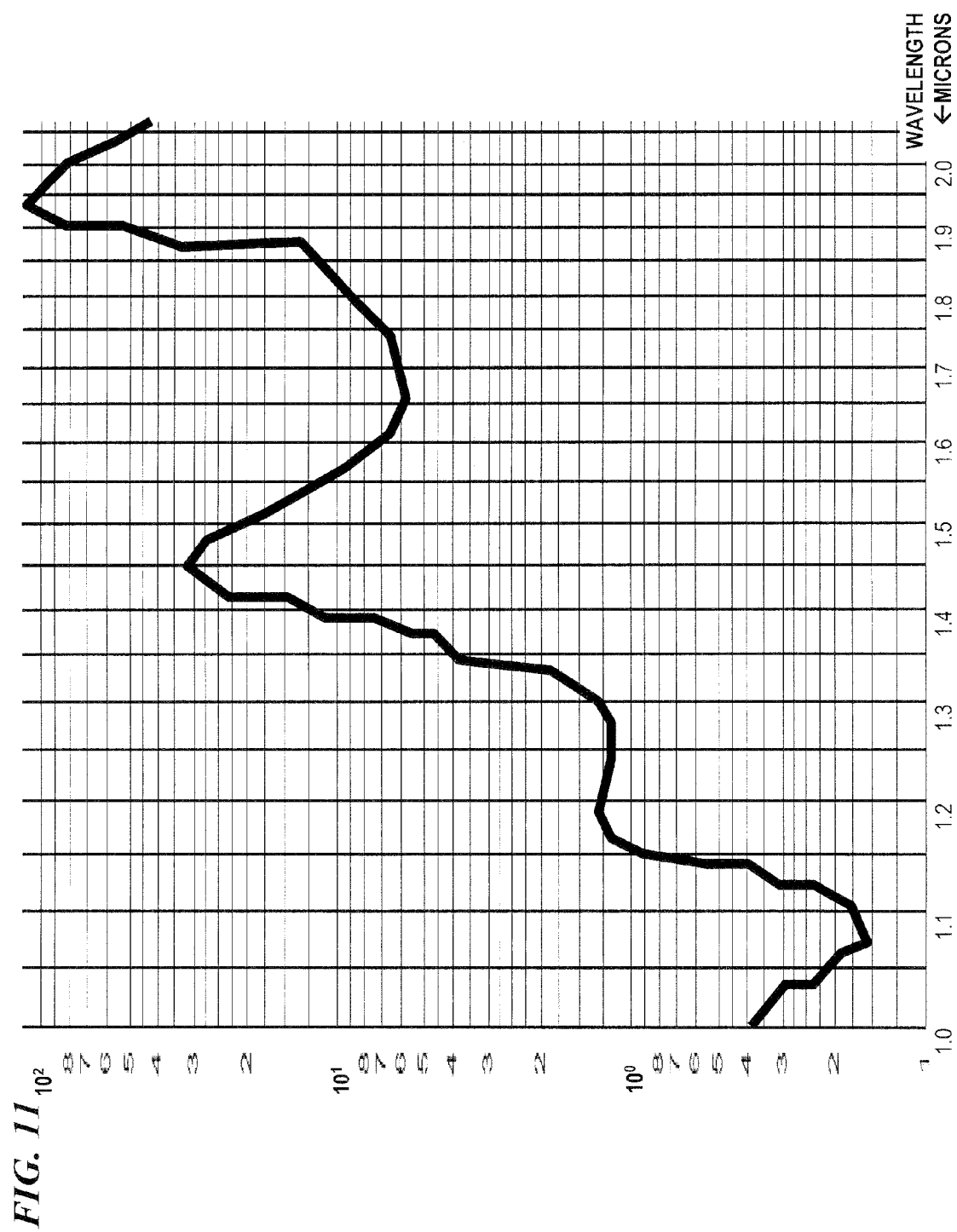
FIG. 11 is a graph of a water absorption factor of light at wavelengths between 1.0 and 2.1 microns.

FIG. 11 is a graph of the raw data used to compute the absorption curve labeled Kou et al. in FIG. 10. This graph is based on data from Kou, L., D. Labrie, and P. Chylek, "Refractive indices of water and ice in the 0.65-2.5-μm spectral range," *Appl. Opt.*, 32, 3531-3540, 1993. Other sources provide similar data, for example, Bashkato, A., Genina, E., Kochubey, E., Kamenskikh, T., and Tuchin, V, "Optical Clearing of Human Eye Sclera," *Proc. Of SPIE, Vol.* 7163.

In some embodiments, the present invention provides an apparatus to aid in the treatment of a vision problem of an eye of a person, wherein the eye has an anteroposterior axis extending from the eye's anterior surface to the eye's fovea. The apparatus includes an ocular unit having an optical path 199 that is substantially transparent (i.e., transmitting at least 50% of incident light) to at least some infrared wavelengths of light between about 1000 nm and about 2000 nm, wherein the ocular unit has a light-receiving anterior end closest to the eye's anterior surface and extends to a posterior end, wherein the posterior end is closer to the fovea than to the eye's anterior surface, and wherein the ocular unit has an a secure-placement feature that is configured to be secured to an anatomical feature of the eye.

In some embodiments, the ocular unit extends across, and replaces, more than 90% of the optical path of the eye of the person, in order to provide an infrared-transparent optical path that is far more transparent to the wavelengths of the nerve-stimulation wavelengths of the optical stimulation signal light 130 than would have been the normal components of the eye.

In some embodiments, the ocular unit transmits out the posterior end more than 30% of infrared signal light that is incident on the anterior end and that has wavelengths in a range between about 1800 and about 2000 nm. In some embodiments, the ocular unit transmits out the posterior end more than 30% of infrared light that is incident on the anterior end and that has wavelengths in a range between about 1000 and about 1200 nm. In some embodiments, the ocular unit transmits out the posterior end more than 30% of infrared light that is incident on the anterior end and that has wavelengths in a range between about 1200 and about 1400 nm. In some embodiments, the ocular unit transmits out the posterior end more than 30% of infrared light that is incident on the anterior end and that has wavelengths in a range between about 1400 and about 1600 nm. In some embodiments, the ocular unit transmits out the posterior end more than 30% of infrared light that is incident on the anterior end and that has wavelengths in a range between about 1600 and about 1800 nm. In some embodiments, the ocular unit transmits out the posterior end more than 30% of infrared light that is incident on the anterior end and that has wavelengths in a range between about 2000 and about 2500 nm. In some embodiments, the ocular unit transmits out the posterior end more than 30% of infrared light that is incident on the anterior end and that has wavelengths in a range between about 2500 and about 3000 nm. In some embodiments, the ocular unit transmits out the posterior end more than 50% of infrared light that is incident on the anterior end and that has wavelengths in one or more of the above-listed ranges.

In some embodiments, the ocular unit transmits out the posterior end more than 60% of infrared light that is incident on the anterior end and that has wavelengths in one or more of the wavelength ranges of between about 1000 to about 1200 nm, between about 1200 and about 1400 nm, between about 1400 and about 1600 nm, between about 1600 and about 1800 nm, between about 1800 and about 2000 nm, between about 2000 and about 2500 nm, and between about 2500 and about 3000 nm. In some embodiments, the ocular unit transmits out the posterior end more than 70% of infrared light that is incident on the anterior end and that has wavelengths in one or more of the wavelength ranges of between about 1000 to about 1200 nm, between about 1200 and about 1400 nm, between about 1400 and about 1600 nm, between about 1600 and about 1800 nm, between about 1800 and about 2000 nm, between about 2000 and about 2500 nm, and between about 2500 and about 3000 nm. In some embodiments, the ocular unit transmits out the posterior end more than 80% of infrared light that is incident on the anterior end and that has wavelengths in one or more of the wavelength ranges of between about 1000 to about 1200 nm, between about 1200 and about 1400 nm, between about 1400 and about 1600 nm, between about 1600 and about 1800 nm, between about 1800 and about 2000 nm, between about 2000 and about 2500 nm, and between about 2500 and about 3000 nm. In some embodiments, the ocular unit transmits out the posterior end more than 90% of infrared light that is incident on the anterior end and that has wavelengths in one or more of the wavelength ranges of between about 1000 to about 1200 nm, between about 1200 and about 1400 nm, between about 1400 and about 1600 nm, between about 1600 and about 1800 nm, between about 1800 and about 2000 nm, between about 2000 and about 2500 nm, and between about 2500 and about 3000 nm. In some embodiments, the ocular unit transmits out the posterior end more than half of infrared light that is incident on the anterior end and that has wavelengths in two or more of the wavelength ranges of between about 1000 to about 1200 nm, between about 1200 and about 1400 nm, between about 1400 and about 1600 nm, between about 1600 and about 1800 nm, between about 1800 and about 2000 nm, between about 2000 and about 2500 nm, and between about 2500 and about 3000 nm.

In some embodiments of the apparatus, the ocular unit includes a thermoplastic material. In some embodiments of the apparatus, the ocular unit includes a biocompatible material. In some embodiments of the apparatus, the ocular unit includes a thermoplastic and biocompatible material. In some embodiments, this material transmits to the posterior end more than half of infrared light having wavelengths between about 1800 and about 2000 nm that is incident on the anterior end. In some embodiments, the material is substantially transparent to other wavelengths in addition to wavelengths between about 1800 and about 2000 nm.

In some embodiments of the apparatus, the biocompatible material includes poly(methyl methacrylate) (PMMA).

In some embodiments of the apparatus, the ocular unit includes a substantially cylindrical-shaped material from the anterior end to the posterior end, and wherein the posterior end of the material has a diameter substantially equal to a diameter of the anterior end of the material.

In some embodiments of the apparatus, the ocular unit includes a substantially conical-shaped material from the anterior end to the posterior end, wherein the posterior end of the material has a diameter that is larger than a diameter of the anterior end of the material.

In some embodiments of the apparatus, the anterior end of the ocular unit is shaped to form a lens to focus the infrared light on nerves of the retina.

In some embodiments of the apparatus, at least part of the ocular unit includes a hollow portion filled with a gas. In some embodiments, the gas is an inert gas having a pressure of less than or equal to about 1000 Torr. In some embodiments, the gas pressure is less than or equal to about 760 Torr. In some embodiments, the gas is under a vacuum of less than about 500 Torr. In some embodiments, at least one end of the hollow portion is shaped to form a lens to focus the infrared light on nerves of the retina.

In some embodiments of the apparatus, the anterior end of the ocular unit extends to through the anterior of the eye replacing at least part of the eye's cornea, and wherein the ocular unit is securely sealed to the sclera.

In some embodiments of the apparatus, the anterior end of the ocular unit is posterior to the eye's cornea and the ocular unit is secured internal to the eye.

In some embodiments of the apparatus, the ocular unit has at least one indicia mark to facilitate detection of the eye's position.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A system to aid in the treatment of a vision problem of an eye of a person, wherein the eye has an anteroposterior axis extending from the eye's anterior surface to the eye's retina, the system comprising:
    an ocular unit configured to be implanted at least in part within the eye, wherein the ocular unit has an optical path that is substantially transparent to at least some infrared wavelengths of light between about 1000 nm and about 1900 nm, wherein the ocular unit, when implanted at least in part within the eye, has a light-receiving anterior end closest to the eye's anterior surface, and extends to a posterior end, wherein the posterior end is within about 2 mm of the eye's retina, wherein the posterior end of the ocular unit is shaped so as to have a substantially constant spacing from the ganglion layer of the retina of the eye, and wherein the ocular unit has a secure-placement feature that is configured to be secured to an anatomical feature of the eye;
    a camera, located external to the eye of the person, that generates an image signal representative of a scene;
    an image processor operatively coupled to the camera to receive the image signal and configured to generate a pulse-control signal representing pulse parameters that are based on the image signal; and
    a light source operatively coupled to the image processor to receive the pulse-control signal and configured to generate a spatial pattern of pulsed infrared light signals that is transmitted through the ocular unit when the ocular unit is implanted at least in part within the eye, wherein the spatial pattern of pulsed infrared light signals is configured to trigger a nerve-action potential response in nerves of a retina layer of the eye of the person, and wherein the pulsed infrared light signals generated by the light source have wavelengths between about 1810 nm and about 1900 nm.

2. The system of claim 1, wherein the ocular unit includes a thermoplastic, biocompatible material that transmits to the posterior end more than half of infrared light having wavelengths between about 1800 and about 1900 nm that is incident on the anterior end.

3. The system of claim 2, wherein the biocompatible material includes poly(methyl methacrylate) (PMMA).

4. The system of claim 1, wherein the ocular unit includes an optical path in a material having substantially cylindrical-shaped sides from the anterior end to the posterior end, and wherein the posterior end of the material has a diameter substantially equal to a diameter of the anterior end of the material.

5. The system of claim 1, wherein the ocular unit includes a tapered material from the anterior end to the posterior end, and wherein the posterior end of the tapered material has a diameter that is larger than a diameter of the anterior end of the material.

6. The system of claim 1, wherein the anterior end of the ocular unit is shaped to form a lens to focus the infrared light on nerves of the retina when the ocular unit is implanted at least in part within the eye.

7. The system of claim 1, wherein at least part of the ocular unit includes an enclosed hollow portion.

8. The system of claim 1, wherein at least part of the ocular unit includes an enclosed hollow portion filled with a gas, and wherein the gas is an inert gas having a pressure of no more than about 1000 Torr.

9. The system of claim 1, wherein at least part of the ocular unit includes an enclosed hollow portion filled with a gas, and wherein at least one end of the hollow portion is shaped to form a lens to focus the infrared light on nerves of the retina when the ocular unit is implanted at least in part within the eye.

10. The system of claim 1, wherein, when the ocular unit is secured to an anatomical feature of the eye, the anterior end of the ocular unit extends through the anterior of the eye replacing at least part of the eye's cornea, and wherein the ocular unit is sealed securely to the sclera.

11. The system of claim 1, wherein the anterior end of the ocular unit is posterior to the eye's cornea when the ocular unit is implanted at least in part within the eye.

12. The system of claim 1, wherein the ocular unit has at least one indicia mark to facilitate detection of the eye's position when the ocular unit is implanted at least in part within the eye.

13. The system of claim 1, wherein, when implanted at least in part within the eye, the posterior end of the ocular unit is located within about 1 mm of the retina.

14. A system to aid in the treatment of a vision problem of an eye of a person, wherein the eye has an anteroposterior axis extending from the eye's anterior surface to the eye's retina, the system comprising:
   means for forming an optical path inside the person's eye, wherein the means for forming the optical path is substantially transparent to at least some infrared wavelengths of light between about 1000 nm and about 1900 nm, wherein the means for forming the optical path, when implanted at least in part within the eye, has a light-receiving anterior end closest to the eye's anterior surface, and extends to a posterior end, wherein the posterior end is within about 2 mm of the retina of the eye, and wherein the posterior end of the means for forming the optical path is shaped so as to have a substantially constant spacing from the ganglion layer of the retina of the eye;
   means for securing the means for forming the optical path to an anatomical feature of the eye;
   a camera, located external to the eye of the person, that generates an image signal representative of a scene;
   an image processor operatively coupled to the camera to receive the image signal and configured to generate a pulse-control signal representing pulse parameters that are based on the image signal; and
   a light source operatively coupled to the image processor to receive the pulse-control signal and configured to generate a spatial pattern of pulsed infrared light signals that is transmitted through the means for forming the optical path when implanted at least in part within the eye, wherein the spatial pattern of pulsed infrared light signals is configured to trigger a nerve-action potential response in nerves of a retina layer of the eye of the person, and wherein the pulsed infrared light signals generated by the light source have wavelengths between about 1810 nm and about 1900 nm.

15. The system of claim 14, wherein the means for forming the optical path further includes means for transmitting to the posterior end more than half of infrared light having wavelengths between about 1800 and about 1900 nm that is incident on the anterior end.

16. The system of claim 14, wherein at least a portion of the means for forming the optical path includes a biocompatible material that includes poly(methyl methacrylate) (PMMA).

17. The system of claim 14, wherein the means for forming the optical path includes means for forming an optical path of a material having substantially cylindrical-shaped sides from the anterior end to the posterior end, and wherein the posterior end of the material has a diameter substantially equal to a diameter of the anterior end of the material.

18. The system of claim 14, wherein the means for forming the optical path includes a material having tapered sides from the anterior end to the posterior end, and wherein the posterior end of the material has a diameter that is larger than a diameter of the anterior end of the material.

19. The system of claim 14, wherein, when implanted at least in part within the eye, the posterior end of the ocular unit is located within about 1 mm of the retina.

20. A system to aid in the treatment of a vision problem of an eye of a person, wherein the eye has an anteroposterior axis extending from the eye's anterior surface to the eye's retina, the system comprising:
   an ocular unit configured to be implanted at least in part within the eye, wherein the ocular unit has an optical path that is substantially transparent to at least some infrared wavelengths of light between about 1000 nm and about 1900 nm, wherein the ocular unit, when implanted at least in part within the eye, has a light-receiving anterior end closest to the eye's anterior surface, and extends to a posterior end, wherein the posterior end is within about 2 mm of the retina of the eye, and wherein the posterior end of the ocular unit is shaped so as to have a substantially constant spacing from the ganglion layer of the retina of the eye;
   means for securing the ocular unit to an anatomical feature of the eye;
   a camera, located external to the eye of the person, that generates an image signal representative of a scene;
   an image processor operatively coupled to the camera to receive the image signal and configured to generate a pulse-control signal representing pulse parameters that are based on the image signal; and
   a light source operatively coupled to the image processor to receive the pulse-control signal and configured to generate a spatial pattern of pulsed infrared light signals that is transmitted through the ocular unit when the ocular unit is implanted at least in part within the eye, wherein the spatial pattern of pulsed infrared light signals is configured to trigger a nerve-action potential response in nerves of a retina layer of the eye of the person, and wherein the pulsed infrared light signals generated by the light source have wavelengths between about 1810 nm and about 1900 nm.

21. The system of claim 20, wherein at least part of the ocular unit includes an enclosed hollow portion.

22. The system of claim 20, wherein the ocular unit includes a tapered material from the anterior end to the posterior end, and wherein the posterior end of the tapered material has a diameter that is larger than a diameter of the anterior end of the material.

23. The system of claim 20, wherein the anterior end of the ocular unit is shaped to form a lens to focus the infrared light on nerves of the retina when the ocular unit is implanted at least in part within the eye.

24. The system of claim 20, wherein the ocular unit has at least one indicia mark to facilitate detection of the eye's position when the ocular unit is implanted at least in part within the eye.

25. The system of claim 20, wherein, when implanted at least in part within the eye, the posterior end of the ocular unit is located within about 1 mm of the retina.

* * * * *